United States Patent [19]
Maeda et al.

[11] Patent Number: 5,774,222
[45] Date of Patent: Jun. 30, 1998

[54] MANUFACTURING METHOD OF SEMICONDUCTOR SUBSTRATIVE AND METHOD AND APPARATUS FOR INSPECTING DEFECTS OF PATTERNS ON AN OBJECT TO BE INSPECTED

[75] Inventors: Shunji Maeda; Yasuhiko Nakayama; Minoru Yoshida, all of Yokohama; Hitoshi Kubota; Kenji Oka, both of Fujisawa, all of Japan

[73] Assignee: Hitachi, Ltd., Tokyo, Japan

[21] Appl. No.: 539,886

[22] Filed: Oct. 6, 1995

[30] Foreign Application Priority Data

Oct. 7, 1994 [JP] Japan .................................. 6-268130

[51] Int. Cl.[6] .............................................. G01N 21/88
[52] U.S. Cl. ......................... 356/394; 356/237; 250/548
[58] Field of Search .................................. 356/237, 239, 356/394, 400, 401, 399; 250/548; 355/53, 77

[56] References Cited

U.S. PATENT DOCUMENTS 5,479,252  12/1995  Worster et al. ......................... 356/237

Primary Examiner—Hoa Q. Pham
Attorney, Agent, or Firm—Antonelli, Terry, Stout & Kraus, LLP

[57] ABSTRACT

A pattern detection method and apparatus thereof for inspecting with high resolution a micro fine defect of a pattern on an inspected object and a semiconductor substrate manufacturing method and system for manufacturing semiconductor substrates such as semiconductor wafers with a high yield. A micro fine pattern on the inspected object is inspected by irradiating an annular-looped illumination through an objective lens onto a wafer mounted on a stage, the wafer having micro fine patterns thereon. The illumination light may be circularly or elliptically polarized and controlled according to an image detected on the pupil of the objective lens and image signals are obtained by detecting a reflected light from the wafer. The image signals are compared with reference image signals and a part of the pattern showing inconsistency is detected as a defect so that simultaneously, a micro fine defect or defects on the micro fine pattern are detected with high resolution. Further, process conditions of a manufacturing line are controlled by analyzing a cause of defect and a factor of defect which occurs on the pattern.

38 Claims, 30 Drawing Sheets

PLAIN OF OBJECT
TO BE INSPECTED

A-A' PART SIGNAL WAVEFORM

A-A' PART SIGNAL WAVEFORM

A-A' PART DETECTION WAVEFORM

| ROTATION ANGLE (deg.) | DETECTED INTENSITY | | |
|---|---|---|---|
| | IN CIRCULAR-POLARIZED ILLUMINATION | LINEAR POLARIZATION (S POLARIZATION) | RANDOM POLARIZATION |
| 0.0 | 1830.0 | 223.4 | 973 |
| 15.0 | 1870.0 | 653.5 | 1265 |
| 30.0 | 1970.0 | 1413.2 | 1809 |
| 45.0 | 2090.0 | 1618.7 | 2081 |
| 60.0 | 2220.0 | 1121.1 | 1889 |
| 75.0 | 2380.0 | 524.1 | 1277 |
| 90.0 | 2510.0 | 261.9 | 981 |
| 105.0 | 2600.0 | 567.9 | 1153 |
| 120.0 | 2550.0 | 1154.3 | 1637 |
| 135.0 | 2380.0 | 1469.9 | 1977 |
| 150.0 | 2170.0 | 1163.9 | 1725 |
| 165.0 | 2000.0 | 560.4 | 1205 |
| 180.0 | 1850.0 | 240.5 | 937 |
| λ/4 WAVE-LENGTH PLATE | USE | NON-USE | NON-USE |

| ANGLE | CIRCULAR POLARIZATION | CIRCULAR POLARIZATION (ANNULAR LOOPED) | S POLARIZATION |
|---|---|---|---|
| 0 | 50.1 | 62.0 | 6.6 |
| 15 | 51.2 | 56.0 | 21.4 |
| 30 | 50.1 | 51.8 | 60.3 |
| 45 | 46.6 | 47.8 | 73.0 |
| 60 | 41.0 | 43.0 | 53.1 |
| 75 | 36.9 | 39.0 | 16.8 |
| 90 | 30.9 | 36.9 | 6.9 |
| 105 | 29.9 | 43.8 | 22.4 |
| 120 | 30.5 | 45.8 | 56.0 |
| 135 | 38.5 | 54.0 | 74.0 |
| 150 | 44.5 | 60.1 | 53.0 |
| 165 | 48.2 | 64.0 | 18.7 |
| 180 | 55.4 | 68.0 | 6.6 |

MANUFACTURING METHOD OF SEMICONDUCTOR SUBSTRATIVE AND METHOD AND APPARATUS FOR INSPECTING DEFECTS OF PATTERNS ON AN OBJECT TO BE INSPECTED

FIELD OF THE INVENTION

The present invention relates to a manufacturing method of a semiconductor substrate such as a semiconductor wafer, a TFT (Thin Film Transistor) liquid crystal substrate, a thin film multi-layer substrate and a printed board, which have respectively micro fine circuit patterns or wiring patterns, at a high yield rate, a method and apparatus for measuring highly precise dimensions of patterns to be inspected, which comprises micro fine circuit patterns or wiring patterns formed on the object to be inspected such as the semiconductor wafer, the TFT liquid crystal substrate, the thin film multi-layer substrate and the printed board and inspecting the patterns on the object to be inspected, a method and apparatus for detecting micro fine defects of the patterns on the object to be inspected, and a microscope to be used in the aforementioned detection method.

BACKGROUND OF THE INVENTION

Recently, the patterns to be inspected, each comprising circuit patterns or wiring patterns formed on, for example, the semiconductor wafer, the TFT liquid crystal substrate, the thin film multi-layer substrate and the printed board have been adapted to be further micro-structured in response to the needs for high density integration. Since the circuit patterns or the wiring patterns are further micro-structured along with high density integration, a defect which should be detected becomes smaller or finer. Detection of such micro fine defects has been an extremely important subject in determination of an integrity of the circuit patterns or the wiring patterns in manufacturing of the circuit patterns or the wiring patterns.

However, the above-described micro structure has been further advanced and detection of micro fine defects of the patterns to be inspected such as the circuit patterns or the wiring patterns has reached the limit of resolution of the imaging optical system, and therefore essential improvement of the resolution has been demanded.

A prior art apparatus for essentially improving the resolution is disclosed in Japanese Patent Laid-Open No. Hei 5-160002. In this document, there is disclosed a pattern inspection apparatus which comprises an illumination arrangement for providing an annular-looped diffusion illumination formed with arrays of a plurality of virtual spot light sources for micro fine circuit patterns which is formed on a mask, through light source space filters, a light receiving arrangement having an optical pupil which sufficiently introduces a diffraction light from the micro fine pattern, which passes through or reflected from a mask which is almost uniformly diffusion-illuminated by the illumination arrangement and has imaging space filters for shutting off at least part of 0th order diffraction light or low order diffraction light of this introduced light, to obtain image signals by receiving the circuit pattern imaged through the optical pupil, and a comparison arrangement for comparing the image signals obtained by the light receiving arrangement with mask pattern data or wafer pattern data or data from a transfer simulator to inspect the pattern. In this document, there is also disclosed a method for controlling a shape of a light source apace filter and an imaging space filter in accordance with the pattern shape data.

However, there has been a problem that, though, in the above-described prior art with respect to detection of a defect of the micro fine pattern. That is, although a defect of the micro fine pattern is detected by applying the annular-looped diffusion illumination to the micro fine pattern on the object to be inspected and sufficiently introducing the diffraction light from the micro fine pattern into the opening (pupil) of the objective lens to obtain high resolution image signals, full consideration has not been taken for the point that a micro fine defect should be detected with high reliability in response to various micro fine patterns existing on the object to the inspected.

Further, full consideration has also not been given for manufacturing semiconductor substrates having micro fine patterns such as a semiconductor wafer, a TFT liquid crystal substrate, a thin film multi-layer substrate and a printed board with reduced defects and high yield rate.

SUMMARY OF THE INVENTION

An object of the present invention is to solve the above problems of the prior art and to provide a method for manufacturing semiconductor substrates which is adapted to manufacture semiconductor substrates such as, for example, a semiconductor wafer, a TFT liquid crystal substrate, a thin film multi-layer substrate and a printed board, each having micro fine patterns, in a high yield rate.

Another object of the present invention is to provide a pattern detection method for detecting a pattern on an object to be inspected and an apparatus thereof (microscope system) which are adapted to detect a defect of a micro fine pattern with high reliability in response to various micro fine patterns provided on objects to be inspected such as a semiconductor wafer, a TFT liquid crystal substrate, a thin film multi-layer substrate, and a printed board.

A further another object of the present invention is to provide a method and an apparatus for inspecting a defect of a pattern on the object to be inspected which are adapted to inspect a micro fine defect of a micro fine pattern with high reliability in response to various micro fine patterns provided on objects to be inspected such as a semiconductor wafer, a TFT liquid crystal substrate, a thin film multi-layer substrate, and a printed board.

To achieve the above objects, a semiconductor substrate manufacturing method for manufacturing semiconductor substrates each having patterns formed by a manufacturing line comprising various process units, according to the present invention comprises: a history data or data base build-up step for building up history data or data base which shows a relation of causes and effects by accumulating in advance the history data or data base showing the relation of defect information of a pattern which appears on the semiconductor substrate and a cause of defect or a factor of defect which causes a defect of the pattern in the manufacturing line; a defect inspection step for detecting the defect information of the pattern by comparing image signals of the pattern on the semiconductor substrate with image signals of the reference pattern, for the semiconductor substrate which has reached a specified position of the manufacturing line; a defect analyzing step for analyzing a cause of defect or a factor of defect which causes a defect of the pattern in the manufacturing line located at an upper stream from the specified position of the manufacturing line, according to the defect information of the pattern detected in the defect inspection step and the history data or the data base which shows the relation of causes and effects, built up in the history data or data base build-up step; and a process condition control step for controlling process conditions in the above-described upper stream manufacturing line to eliminate the cause of defect or the factor of defect analyzed in the defect analyzing step.

With the configuration described above, the present invention enables inspection of micro fine defects with high resolution and high sensitivity on semiconductor substrates such as the semiconductor wafer, the TFT substrate, the thin film multi-layer substrate and the printed board each having micro fine patterns (for example, patterns the pitch of which is 1 μm or under (0.8 to 0.4 μm)), to reduce the number of micro fine defects on the semiconductor substrates by feeding back the results of inspection to the manufacturing processes for semiconductor substrates, and to manufacture the semiconductor substrates having micro fine patterns with a high yield rate.

According to the present invention, for materializing a manufacturing method of the semiconductor substrate, a method and apparatus for detecting a defect of the patterns on the object to be inspected are adapted to detect the pattern on the object to be inspected according to the image signals of the pattern on the object to be inspected which are obtained by concentrating an annular-looped diffusion illumination light formed by a plurality of virtual spot light sources and irradiating the illumination light onto the pattern on the object to be inspected through the pupil of the objective lens. The above configuration enables sufficient introduction of the reflected light which is obtained by slantly or obliquely introducing a focused illumination light from, for example, the annular-looped illumination onto a semiconductor substrate (object to be inspected), into the opening (pupil) of the objective lens and consequently obtain image signals of a pattern having a sufficient resolution, identify the reflected light by monitoring an image on the pupil plane of the objective lens, and detect the image signals of the pattern with the sufficient resolution and a large depth of the focus under an optimum condition at all times in response to a micro fine pattern by, for example, controlling the annular-looped illumination. By detecting a localization distribution or an intensity distribution of the reflected light from the image of the pupil plane (Fourier transformation plane) and controlling the annular-looped illumination in accordance with the localization distribution or the intensity distribution (corresponding to the density of pattern) of the detected diffraction light, the pattern can be sufficiently inspected with a normal resolution by the annular-looped illumination under the preset condition since the pattern density is not so high in a case of, for example, a 4 Mb DRAM memory device and the pattern can be inspected with the annular-looped illumination which provides a higher resolution under the preset condition in a case of, for example, a 16 Mb DRAM memory device. In addition, the pattern can be inspected with high resolution by using the annular-looped illumination under the preset condition since the pattern density is high at, for example, the cell part of the memory device and the pattern can be inspected at a high speed by using a normal illumination since the inspection sensitivity can be lowered in a rough area other than the cell part.

Furthermore, for implementing the above-described semiconductor substrate manufacturing method, a method and apparatus for inspecting a defect of a pattern on the object to be inspected according to the present invention are adapted to concentrate and irradiate the annular-looped diffusion illumination light comprising a number of virtual spot light sources onto the pattern on the object to be inspected through the pupil of the objective lens, compare an image signal obtained therefrom of the pattern on the inspected object with the image signal of the reference pattern, and erase the pattern on the inspected object when these image signals coincide and detect a defect when these image signals do not coincide.

The above-described configuration enables detection of high definition (high resolution) image signals from micro fine patterns and inspection of a defect on the micro fine pattern with high reliability since the high definition image signals can be compared with the high definition reference image signals with respect to a chip or cell.

DESCRIPTION OF THE PREFERRED EMBODIMENTS

Figure 38:
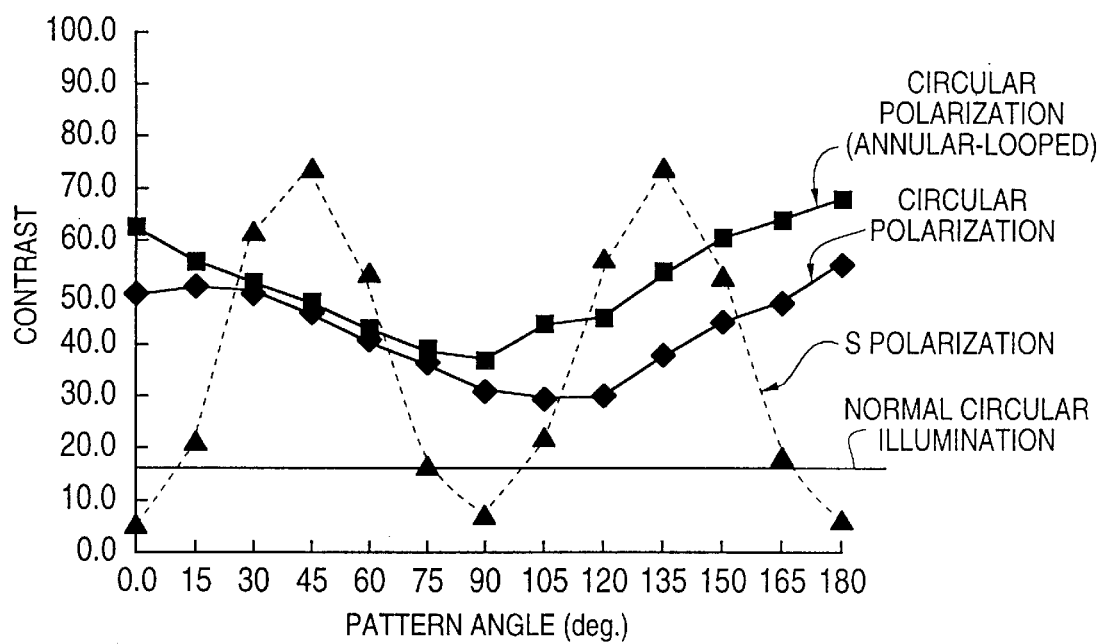
FIG. 38 shows a contrast for a pattern angle in an experimental example for which a state of polarization in the annular-looped illumination is controlled.
Figure 39:
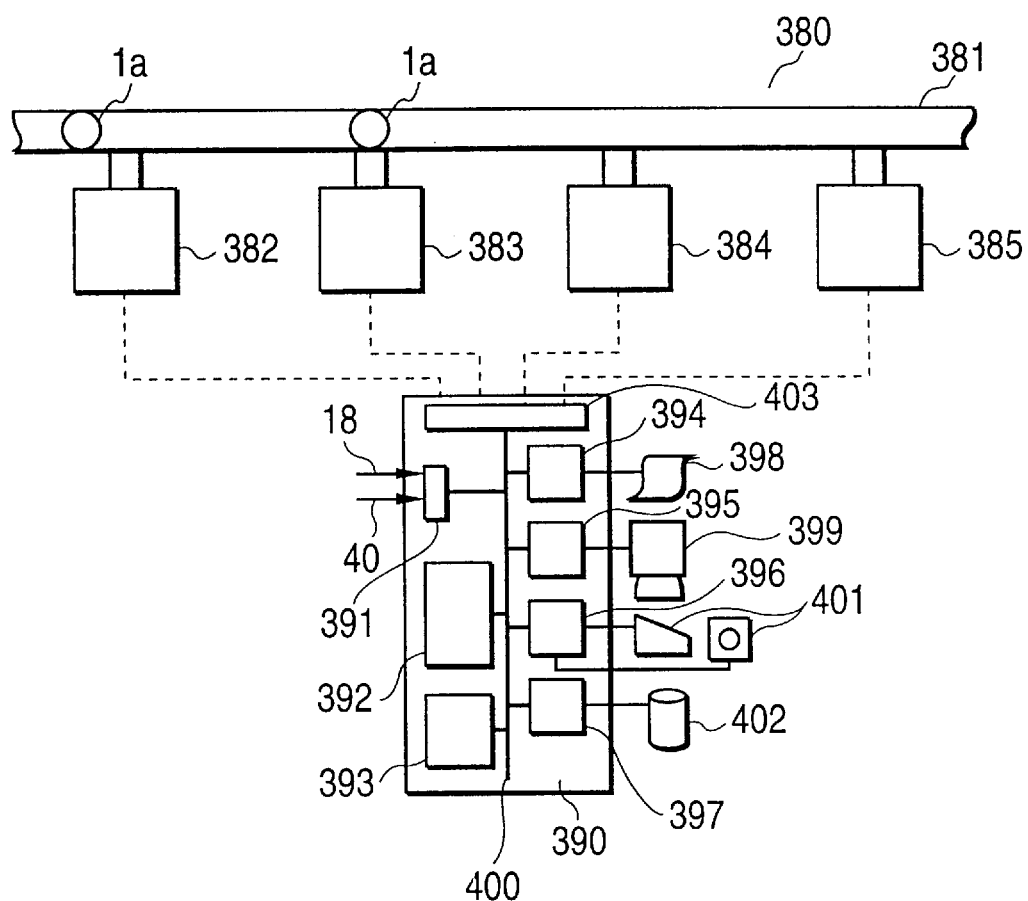
FIG. 39 is a block diagram arrangement for describing manufacturing of semiconductor substrates at a high yield rate by analyzing causes of defect or factors of defect with an analytical computer according to the present invention and feeding back the causes of defect or the factors of defect which has been analyzed to the process units in a manufacturing line.

Referring now to the drawings, like reference numerals are utilized to designate like parts throughout so that detailed description of the like parts are omitted with embodiments according to the present invention for detection of a pattern on an object to be inspected and inspection of a defect on the pattern being described, referring to FIGS. 1 to 39, and an embodiment according to the present invention in which inspection of a defect on the object to be inspected is applied to semiconductor manufacturing processes being described referring to FIG. 39. In the embodiments, an annular-looped illumination (annular-looped diffusion illumination) is utilized for providing substantially uniform illumination in a field of detection of the object to be inspected through an objective lens is described below.

Figure 1:
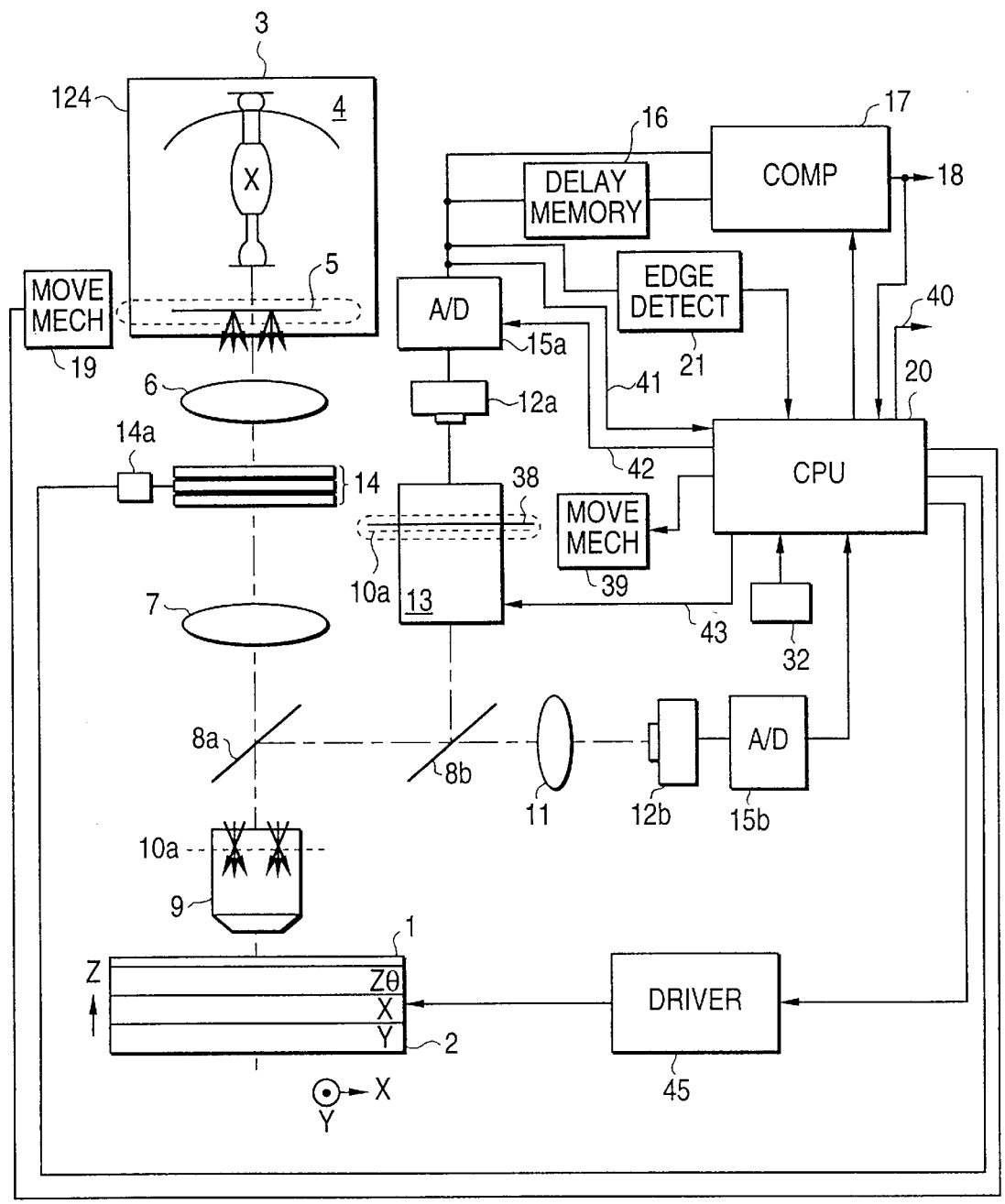
FIG. 1 is a block diagram arrangement showing an embodiment of an inspection apparatus according to the present invention for inspecting a defect of the pattern on the object to be inspected.

FIG. 1 is a block diagram showing a first embodiment of a pattern inspection apparatus using annular-looped illumination according to the present invention comprising an object to be inspected (a pattern to be inspected) 1 such as an LSI wafer for pattern inspection; an XYZθ stage 2 on which the object to be inspected 1 such as the LSI wafer is mounted; a secondary light source for annular-looped illumination which includes a xenon (Xe) lamp 3 for a light source, an elliptic mirror 4 for focusing a light and a disc type mask 5 (secondary light source for annular-looped illumination) for forming an annular-looped illumination (annular-looped diffusion illumination) for forming an annular-looped secondary light source which includes a plurality of virtual spot light sources; an illumination optical system including a collimator lens 6, a light quantity control filter 14 and a condenser lens 7; a pattern detection optical system which includes half mirrors 8a and 8b, an objective lens 9, a focusing lens 11, a zoom lens 13 provided with an attenuation filter 38 on a pupil plane 10b conjugated with the pupil plane 10a of the objective lens 9 and two-dimensional or one-dimensional image sensors 12a and 12b; and an image processing and controlling system for detection of defects, which includes A/D converters 15a and 15b for converting image signals detected from the image sensors 12a and 12b to digital image signals, a delay memory 16 for storing digital image signals obtained from the A/D converter 15a and delaying these image signals, a comparator circuit 17 for comparing delayed digital image signals stored in the delay memory 16 and digital image signals obtained from the A/D converter 15a, an edge detector 21 for detecting an edge of the pattern from the digital image signals obtained from the A/D converter 15a, and a CPU 20 which carries out the control of the disc type mask 5 for forming the annular-looped illumination which is the secondary light source based on a moving mechanism 19 and the control of the attenuation filter 38 based on a moving mechanism 39 in accordance with the digital image signals on the pupil plane 10a of the objective lens 9 obtained from the image sensor 12b, which detects the image of the pupil plane 10a of the objective lens 9 through the A/D converter 15b, carries out the comparison in the comparator circuit 17 in accordance with the edge signal to be detected by the edge detector 21 and carries out the control of the XYZθ stage 2 based on a driver 45.

Figure 23:
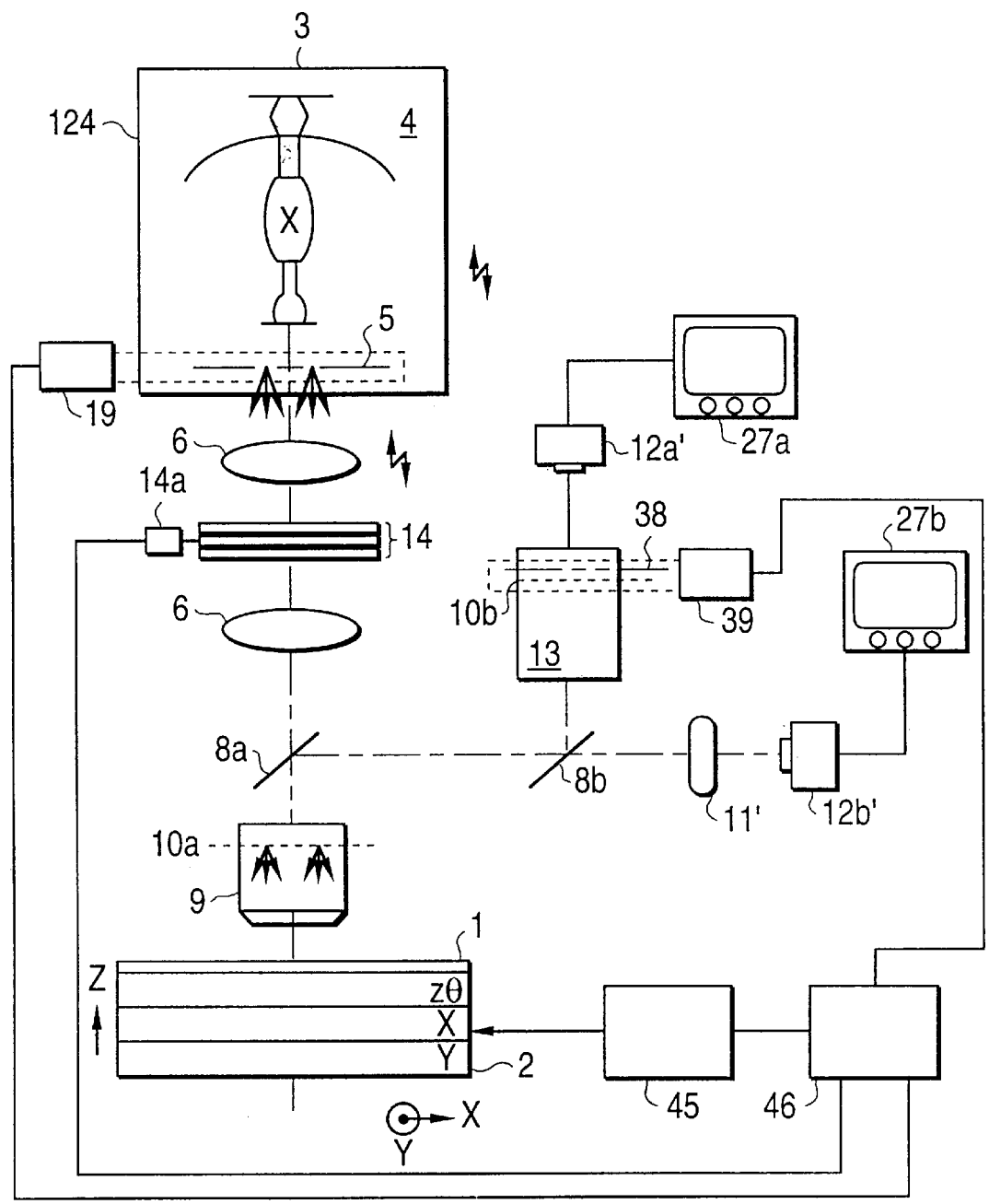
FIG. 23 is a block diagram arrangement showing an embodiment of a microscope system according to the present invention.
Figure 24:
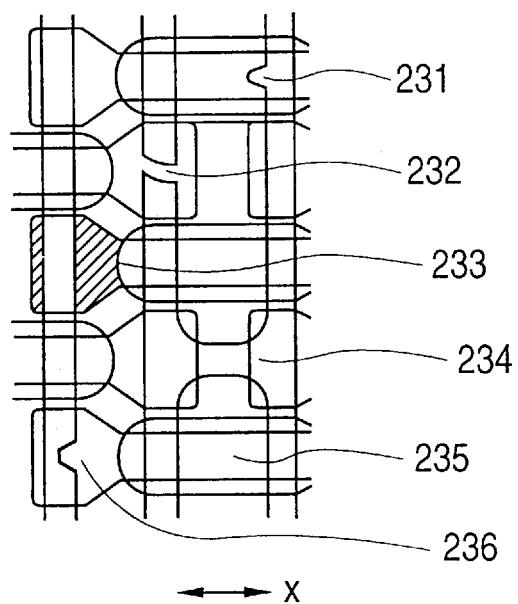
FIG. 24 is a diagram showing various defects in a wafer pattern according to the present invention.

A defect determination output 18 is obtained from the comparator circuit 17 and is also entered into the CPU to be added with a defect occurring position (coordinates) on the object 1 to be inspected and is stored in storage arrangement (not shown) for at least a unit of the inspected object 1 and a unit of a plurality of inspected objects 1 sampled from a specified manufacturing process. Defect information 40 in at least the unit of the inspected object 1 and the process unit of the inspected object 1 sampled from the specified manufacturing process which is stored in this storage means is outputted from the CPU 20. This defect information 40 includes the defect occurring position (coordinates) on the inspected object 1 obtained based on the defect determination output 18 and a type of defect (projection defect 231, chipping defect 236, opening defect 232, short-circuiting defect 234, discoloration defect 233, stain defect 235, etc., as shown in FIG. 24, for example) which is classified according to the defect determination output 18 in the CPU 20 as shown in FIG. 23. The types of these defects need not always be definitely classified.

In FIG. 1, a light house 124 is formed with the Xe lamp 3 which is the primary light source, the elliptic mirror 4 for focusing a light emitted from the Xe lamp 3 and the disc type mask 5 comprising a plurality of virtual spot light sources, for forming the annular-looped illumination as the secondary light source. The moving mechanism 19 is provided to rotate the disc type mask (secondary light source for annular-looped illumination) 5 in steps according to a command from the CPU 20 and to change over a different type annular-looped illumination (if there is no IN a as shown, for example, in FIG. 3, it is similar to normal illumination). The disc type mask 5 is the annular-looped secondary light source formed by a plurality of virtual spot light sources and an annular-looped diffusion illumination is obtained from this annular-looped secondary light source.

Figure 7:
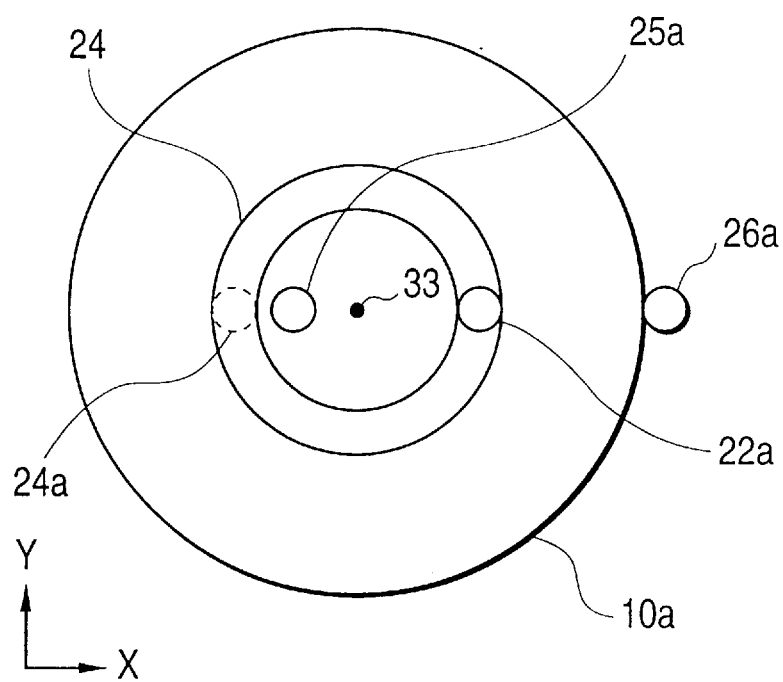
FIG. 7 is an X-Y plan view on the pupil of the objective lens, showing 0th order diffraction light and first order diffraction light which are produced in the X axis direction from the grid pattern shown in FIG. 6 by casting the annular-looped illumination onto the grid pattern to be incident onto the pupil of the objective lens.
Figure 9:
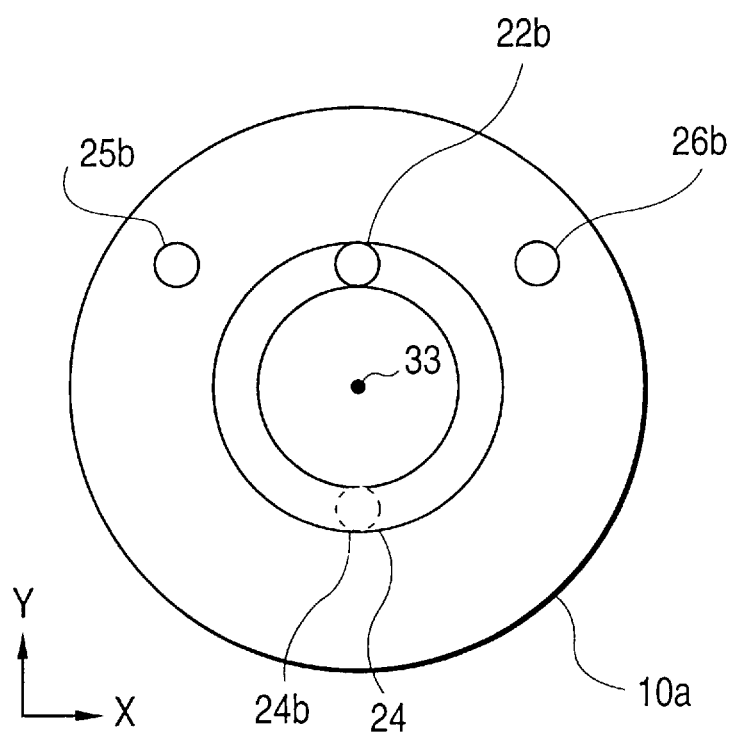
FIG. 9 is an X-Y plan view on the pupil of the objective lens, showing 0th order diffraction light and first order diffraction light which are produced in the Y axis direction from the grid pattern shown in FIG. 6 by casting the annular-looped illumination onto the grid pattern to be incident onto the pupil of the objective lens.
Figure 10:
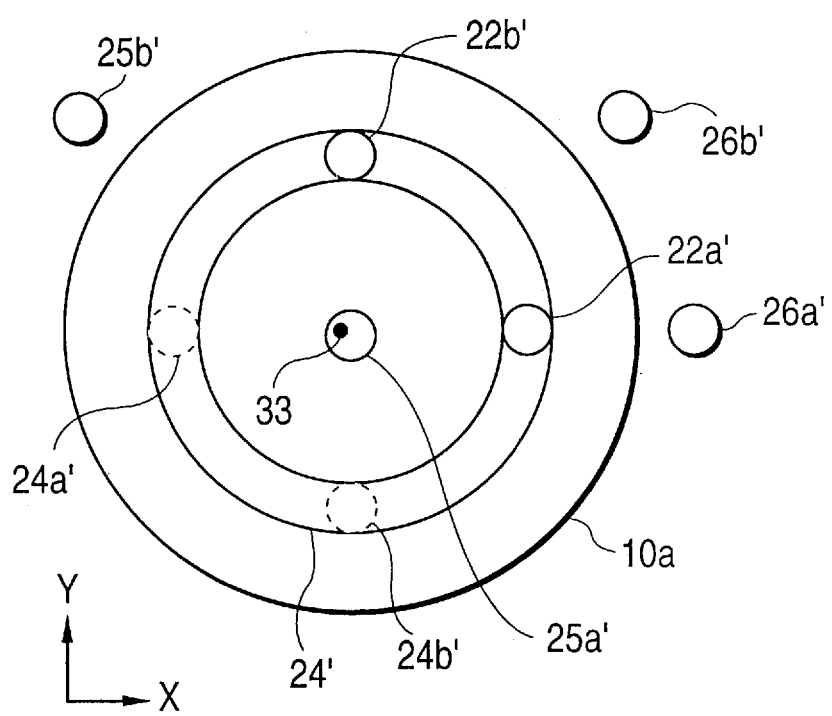
FIG. 10 is an X-Y plan view on the pupil of the objective lens, showing 0th order diffraction light and first order diffraction light which are produced in X and Y axis directions from the grid pattern shown in FIG. 6 by casting the annular-looped illumination onto the grid pattern to be incident onto the pupil of the objective lens.

Accordingly, the annular-looped illumination emitted from the disc type mask (secondary light source for annular-looped illumination) 5 is focused as an incident illumination light 24 onto the pupil 10a of the objective lens 9 through the collimator lenses 6 and 7 as shown in FIGS. 7, 9 and 10, and this focused incident illumination light is focused by the objective lens 9 and irradiated onto the inspected object 1 such as an LSI wafer set on the XYZθ stage 2 (the θ stage not being shown). The light quantity control filter 14 serves to adjust a light quantity to be irradiated onto the inspected object 1. A drive mechanism 14a for driving the light quantity adjusting filter 14 is controlled in accordance with a command from the CPU 20.

A 0th order reflected diffraction light (positive reflection light), and first order and second order reflected diffraction lights at the + and − sides are produced from the pattern on the inspected object 1 such as the LSI wafer. Thus, of the 0th order reflected diffraction light (positive reflection light) and + and − side first order and second order reflected diffraction lights produced as described above, a reflected diffraction light which is introduced into the pupil 10a of the objective lens 9 is reflected from the half mirrors 8a and 8b to be incident onto the pupil 10b of the zoom lens 13 and this reflected diffraction light is focused onto the image sensor 12a by the zoom lens 13. The image sensor 12a receives the reflected diffraction light which is produced from the pattern on the inspected object 1 such as the LSI wafer and introduced to be incident into the pupil 10a of the objective lens 9, and outputs an image signal representing the reflected diffraction light of the pattern of the inspected object 1. The pupil 10a of the objective lens 9 and the pupil 10b of the zoom lens 13 have a conjugating relationship. The 0th order diffraction light introduced into the pupil 10a of the objective lens 9 can be attenuated by the attenuation filter 38 on the pupil 10b of the zoom lens 13 as required.

Figure 13A:
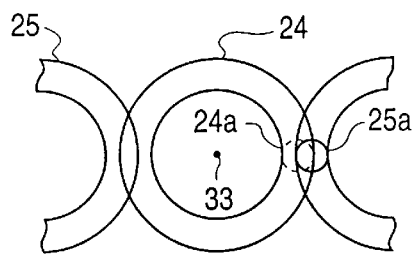
FIGS. 13(a) and 13(b) are illustrations of a linear diagram showing a situation where + first order diffraction light is produced when the annular-looped illumination with the wavelength of λ=0.4 to 0.6 μm and the value σ of 0.60 to 0.40 is cast to a grid pattern of P=0.61 μm.
Figure 13B:
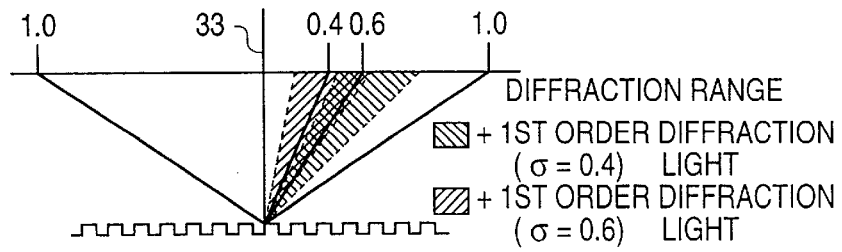

On the other hand, the reflected diffraction light introduced into the pupil 10a of the objective lens 9 is focused onto the image sensor 12b through the focusing lens 11. Accordingly, the image sensor 12b receives the reflected diffraction light introduced into the pupil 10a of the objective lens 9 and outputs the image signal of this reflected diffraction light to permit detection of a state of the reflected diffraction light incident into the pupil 10a of the objective lens 9. In other words, if the periodicity of the pattern on the inspected object 1 such as the LSI wafer changes as shown in FIGS. 13 and 14, the mode of the first order diffraction light to the incident illumination light 24 also changes and the first order diffraction light incident into the pupil 10a of the objective lens 9 changes simultaneously. FIG. 13 shows a case where the density (periodicity) of the pattern on the inspected object 1 is high and FIG. 14 shows a case where the density (periodicity) of the pattern on the inspected object 1 is low. If the pitch P (density or periodicity) of the pattern on the inspected object 1 or the wavelength X of the incident illumination light 24 is changed, it is known from a relation presented by equation 2 that the diffraction angle θ of the first order diffraction light to the incident angle ψ of the incident illumination light 24 changes and the first order diffraction light incident into the pupil 10a of the objective lens 9 also changes.

If the type of the inspected object 1 such as, for example, the LSI wafer is changed, the pitch P (density or periodicity) of the pattern thereon also changes. If the type of the LSI wafer is changed to, for example, 256M DRAM or 64M DRAM, the pitch P (density or periodicity) of the pattern also changes. If the process is changed even though the types are of the same, the density (periodicity) of the pattern may change, for example, the pitch P of the pattern of the inspected object in the wiring process or the diffusion process changes. In one chip on the LSI wafer, the pitches P of the patterns of the memory and the peripheral circuit differ from each other.

It is necessary to change the wavelength λ of the incident illumination light 24 in accordance with the cross sectional structure of the inspected object 1. For example, a thickness of a thin film which forms the inspected object 1 varies and therefore the reflected light from the inspected object is caused to change due to an optical interference in the thin film. To avoid such variation of the reflected light, it is necessary to change the wavelength λ of the incident illumination light 24 to select the wavelength λ of the incident illumination light 24 with which the optical interference hardly occurs in the thin film. For example, as shown in other embodiments described later, the wavelength λ of the incident illumination light 24 can be changed through a wavelength selection filter by using a light source which emits lights, respectively, having a plurality of types of wavelength in the illumination optical system.

If the pitch P (density or periodicity) of the pattern on the inspected object 1 or the wavelength λ of the incident illumination light 24 is changed, the diffraction angle θ of the first order diffraction light to the incident angle ψ of the incident illumination light 24 changes and the first order diffraction light incident into the pupil 10a of the objective lens 9 also changes. Therefore, the value a of the secondary light source for annular-looped illumination, that is, the incident angle ψ of the illumination light 24 to the inspected object 1 should be controlled in accordance with the type or the cross sectional structure of the inspected object 1 so that, particularly, the first order diffraction light of the diffraction lights produced from the inspected object is introduced into the pupil 10a of the objective lens 9 in an optimal condition.

Figure 3:
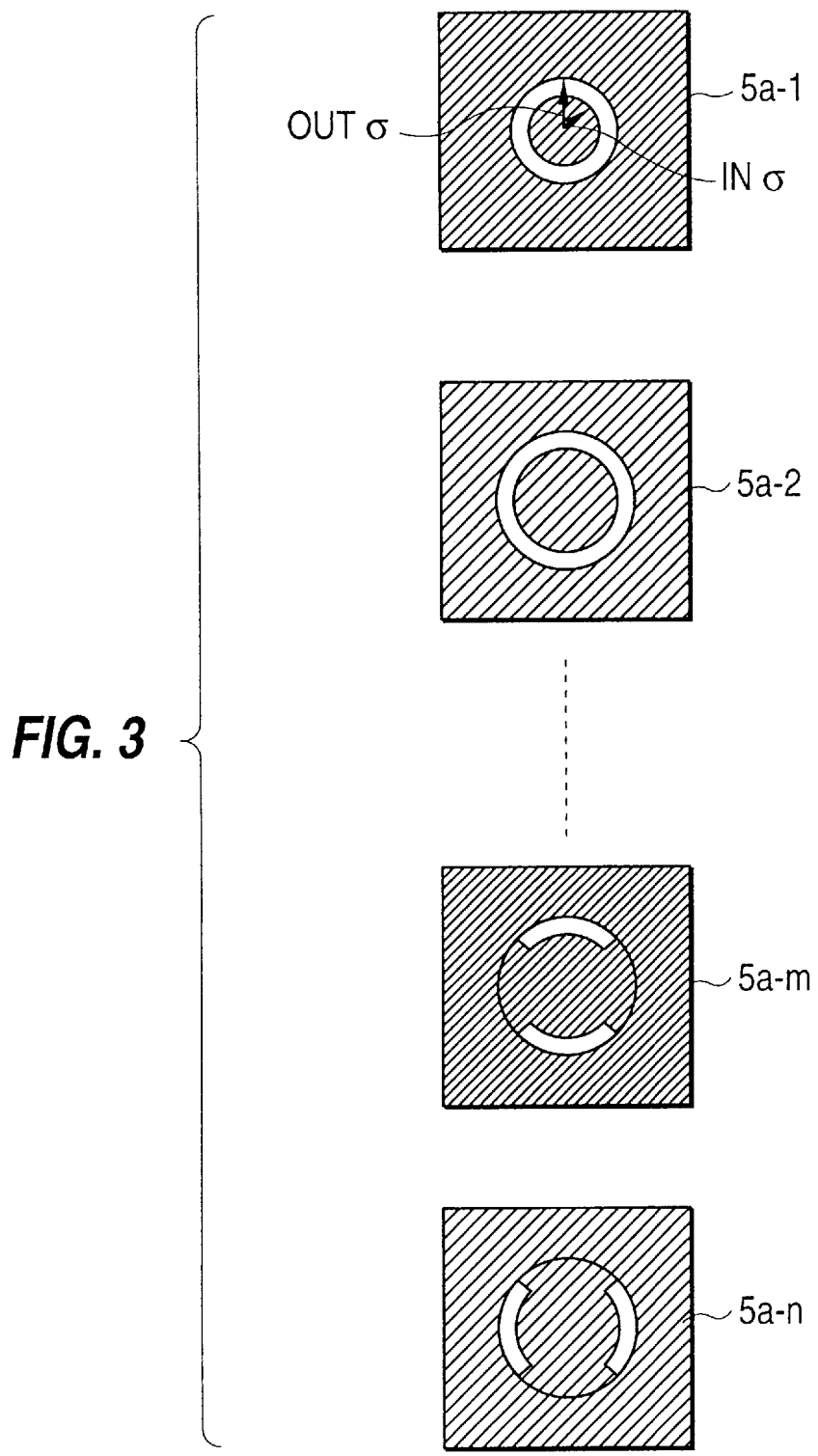
FIG. 3 is a schematic illustration showing in detail the mask element of the disc type mask shown in FIG. 2.
Figure 4:
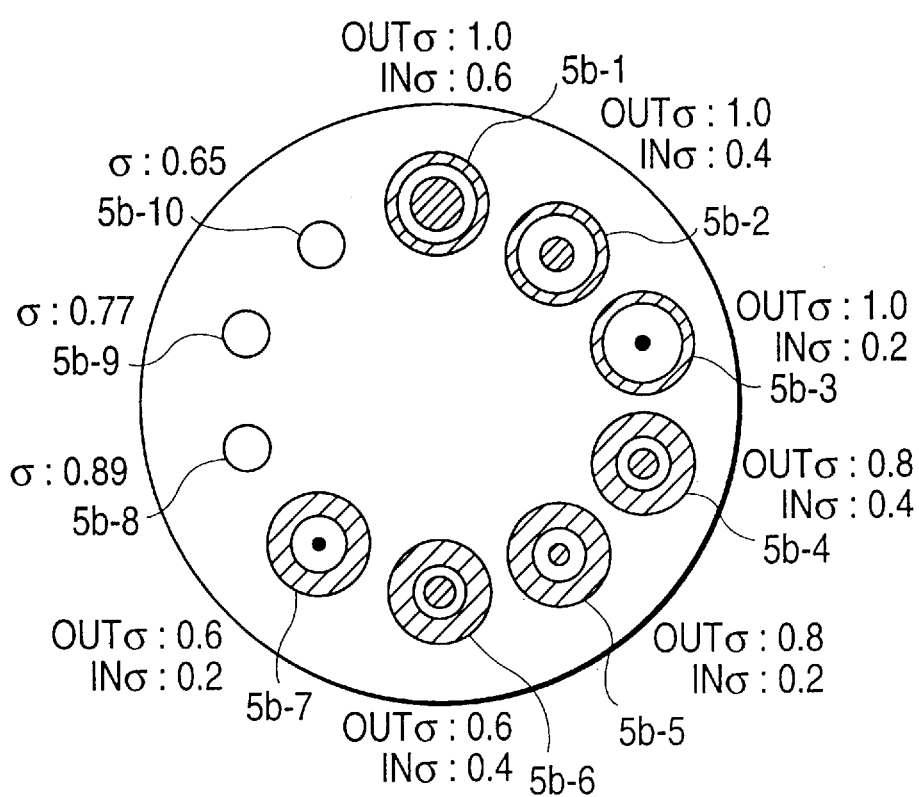
FIG. 4 is a schematic illustration showing further in detail the mask element of the disc type mask shown in FIG. 2.

Therefore, the CPU 20 carries out a Fourier transform image analysis of digital Fourier transform image signals on the pupil 10a (Fourier transform plane) of the objective lens 9 obtained from the image sensor 12b through the A/D converter 15b and edge density determination (periodicity or density determination of the pattern on the inspected object 1) according to the results of this Fourier transform image analysis, and selects the secondary light source 5 (as shown, for example, in FIGS. 3 and 4; FIG. 4 includes an ordinary light source with IN σ of 0) for the optimum annular-looped illumination by driving the moving mechanism 19 so that the digital image signal of the reflected diffraction light introduced into the pupil 10a of the objective lens 9, that is, the 0th order and first order diffraction lights from the pattern on the inspected object 1 are sufficiently introduced into the pupil 10a of the objective lens 9 to obtain faithful image signals from the pattern on the inspected object 1 from the image sensor 12a.

Illumination is the so-called Koehler illumination free of unevenness. Although not shown, the illumination light is focused so that the image of the reflected diffraction light from the pattern on the inspected object 1 such as the LSI wafer is clearly formed in the image sensor 12a. In other words, the pattern (surface) on the inspected object 1 such as the LSI wafer is automatically focused to the detection optical system.

Two-dimensional image signals of the pattern on the inspected object 1 can be obtained from the image sensor 12a by scanning to pick up the pattern image with the image sensor 12a while moving the X stage on which the inspected object 1 such as the LSI wafer is set. In this case, the X stage can be moved in continuous feed, step feed or repeated feed.

The two-dimensional image signals obtained as described above are A/D-converted by the A/D converter 15a, two-dimensional digital image signals are stored in the delay memory 16 to be delayed while inspection of the chip or the cell is repeated, and the delayed two-dimensional digital image signals and the two-dimensional digital image signals outputted from the A/D converter 15a are compared with respect to the chip or the cell by the comparator circuit 17, and unmatched digital image signals are detected as a defect 18.

The above-described comparator circuit 17 is known in the art and therefore a detailed description is omitted and it is briefly described below. This comparator circuit 17 is adapted so that two-dimensional light and dark image signals (digital image signals) obtained from the delay memory 16 and the A/D converter 15a with respect to the patterns on the inspected object 1 which are formed to be identical are differentiation-processed, the positions of two light and dark image signals to be compared are aligned so that the number of pixels whose polarities do not match is not more than a preset value when the polarities of these light and dark image signals obtained from such differentiation processing are compared, a differential image signal of the two light and dark image signals the positions of which are aligned is detected, and a defect is detected by binary-coding this differential image signal with a desired threshold value. The comparison processing in this comparator circuit 17 is described in detail in Japanese Patent Laid-Open No. Hei 3-209843.

The edge detector 21 detects an edge of the pattern on the inspected object 1 according to the two-dimensional digital image signal which is detected by the image sensor 12a and obtained through the A/D converter 15a. The CPU 20 is able to align the positions of two light and dark image signals (digital image signals) in the comparator circuit 17 by fetching the edge information of the pattern on the inspected object 1 detected by the edge detector 21 and feeding back the information to the comparator circuit 17 and compare these signals with respect to the chip and the cell by controlling the timing read out from the delay memory 16.

It is apparent that the comparator circuit 17 is not limited to the above-described configuration and a comparator circuit with another configuration can be used.

A two-dimensional digital image signal at a position on the designated stage coordinates obtained from the A/D converter 15a can be stored in the delay memory 16 and the CPU is able to read out and analyze this signal. Particularly, if the inspected object 1 includes a defect, the characteristics of the defect can be analyzed and therefore the optimum inspection conditions can be found.

Figure 2:
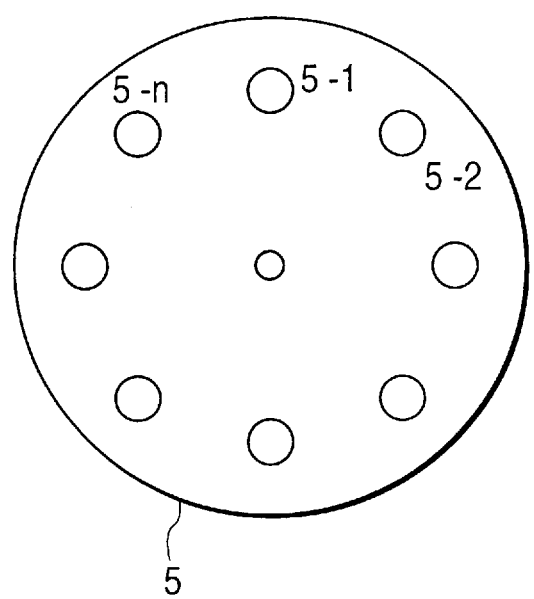
FIG. 2 is a schematic illustration of a disc type mask (annular-looped secondary light source) in the embodiment shown in FIG. 1.

The disc type mask (secondary light source for annular-looped illumination) 5 for forming the annular-looped illumination is now described referring to FIGS. 2 to 5, wherein FIG. 2 is a schematic illustration of the disc type mask (an array of many kinds of mask elements for annular-looped illumination) in the embodiment shown in FIG. 1. FIG. 3 shows a practical embodiment of the disc type mask (an array of many kinds of mask elements for annular-looped illumination) shown in FIG. 2. FIG. 4 shows another practical embodiment of the disc type mask (an array of many kinds of mask elements for annular-looped illumination) shown in FIG. 2 and FIGS. 5(a) and 5(b) are diagrams for illustrating the mask element for one annular-looped illumination shown in FIGS. 3 and 4.

Figure 5A:
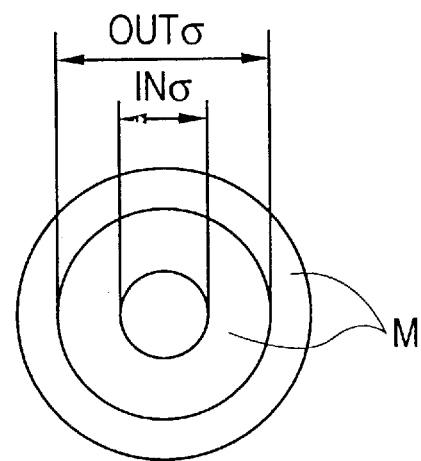
FIGS. 5a and 5b show an illustration showing practical dimensions of the mask element shown in FIG. 4.

As shown in FIG. 2, mask elements 5-1, 5-2, . . . , 5-n, for example, for many types of annular-looped illuminations are provided on the disc type mask 5 and the disc type mask 5 is changed over by the moving mechanism 19 which serves to rotate the disc type mask 5. FIG. 3 shows in detail the mask elements 5-1, 5-2, . . . , 5-n for many types of annular-looped illuminations shown in FIG. 2 with 5a-1, 5a-2, . . . , 5a-n. In FIG. 3, 5a-1 denotes a ring-shaped mask element on which a portion between IN a and OUT a is made to be transparent, 5a-2 shows a ring-shaped mask element on which IN σ and OUT σ are made to be larger than those of 5a-1, and 5a-n shows a ring-shaped mask element in which a portion of a ring-shaped transparent part is shielded.

FIG. 4 shows in detail the mask elements 5-1, 5-2, ..., 5-n for many types of annular-looped illuminations shown in FIG. 2 with 5b-1, 5b-2, 5b-3, 5b-4, 5b-5, 5b-6, 5b-7, 5b-8, 5b-9, and 5a-10. 5b-1 shows a ring-shaped mask element on which a portion between IN σ of 0.6 and OUT σ of 1.0 is made transparent, 5b-2 shows a ring-shaped mask element on which a portion between IN σ of 0.4 and OUT σ of 1.0 is made transparent, 5b-3 shows a ring-shaped mask element on which a portion between IN σ of 0.2 and OUT σ of 1.0 is made transparent, 5b-4 shows a ring-shaped mask element on which a portion between IN σ of 0.4 and OUT σ of 0.8 is made transparent, 5b-5 a ring-shaped mask element on which a portion between IN σ of 0.2 and OUT σ of 0.8 is made transparent, 5b-6 a ring-shaped mask element on which a portion between IN σ of 0.4 and OUT σ of 0.6 is made transparent, and 5b-7 shows a ring-shaped mask element on which a portion between IN σ of 0.2 and OUT σ of 0.6 is made transparent. The ring-shaped mask elements 5b-1 to 5b-7 form the secondary light source for the annular-looped illumination.

In FIG. 4, 5b-8 shows a mask element which is formed with a circular transparent part for which the value σ is 0.89, 5b-9 shows a mask element which is formed with a circular transparent part for which the value σ is 0.77, and 5b-10 shows a mask element which is formed with a circular transparent part for which the value σ is 0.65. These mask elements 5b-8 to 5b-10 form an ordinary secondary light source with different values σ. The value σ of 1.0 indicates that it is equal to an aperture NA (Numerical Aperture): corresponding to the diameter of the pupil) of the objective lens 9.

Figure 5B:
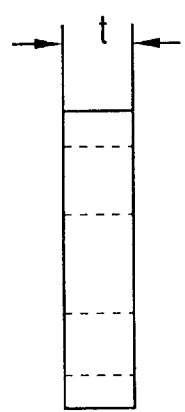

FIGS. 5(a) and 5(b) are diagrams for showing practical dimensions of the ring-shaped mask elements shown in FIG. 4, wherein M is a surface of an opaque mask which shuts off the light and shows IN σ and OUT σ. FIG. 5(b) shows the thickness t of the mask which is assumed as 2.3 mm. The diameters of OUT σ and IN σ of the ring-shaped mask elements of 5b-1 to 5b-7 are shown in Table 1 below.

TABLE 1

| Part No. | Diameter of OUT σ | Diameter of IN σ |
|---|---|---|
| 5b-1 | 5.25 mm | 3.15 mm |
| 5b-2 | 5.25 mm | 2.10 mm |
| 5b-3 | 5.25 mm | 1.05 mm |
| 5b-4 | 4.20 mm | 2.10 mm |
| 5b-5 | 4.20 mm | 1.05 mm |
| 5b-6 | 3.15 mm | 2.10 mm |
| 5b-7 | 3.15 mm | 1.05 mm |

The inside part of IN σ is made to be opaque in the above-described ring-shaped mask elements. When it is made opaque, the light quantity reduces and therefore the inside part of IN σ can be made to be opaque to conform to the patterns on the high density inspected object 1 without substantially reducing the light quantity. The part between IN σ and OUT σ can be substantially transparent. Although, in the above embodiment, the part between IN σ and OUT σ is formed with a ring-shaped transparent member, it is obvious that the part can be formed by arranging a plurality of circular transparent members in the shape of ring.

As described above, many kinds of secondary or virtual light sources can be formed by forming many types of mask elements on the disc type mask 5 and therefore an appropriate incident illumination light for various inspected objects 1 can be obtained. Consequently, the 0th order diffraction light and the first order diffraction light (+ first order diffraction light or − first order diffraction light) obtained from various inspected objects 1 can be introduced into the opening (pupil) 10a of the objective lens 9 and two-dimensional image signals having a sufficient resolution for various inspected objects 1 can be obtained from the image sensor 12a.

Figure 12:
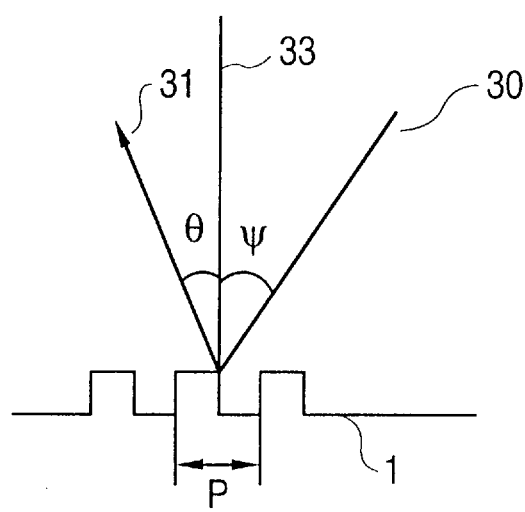
FIG. 12 is an illustration showing the relationship between the incident angle ψ and the diffraction angle θ.

Two-dimensional image signals having a sufficient resolution for a high density pattern on the inspected object can be obtained by using the annular-looped illumination for the following reason. In case of ordinary illumination, the incident angle ψ of an incident illumination light 30 shown in FIG. 12 is approximately 0. In a case that the pitch P of the inspected object 1 is small (in case of a high density pattern), the diffraction angle θ of the 0th order diffraction light (m×0) is equal to the incident angle ψ to be within the pupil 10a of the objective lens 9 for the relation represented by the equation 2. However, the diffraction angles θ of the + first order diffraction light and the − first order diffraction light become large because the above-described pitches P is small, and cannot therefore be introduced into the pupil 10a of the objective lens 9. Accordingly, only the 0th order diffraction light, that is, the light of the DC component, is obtained from the high density pattern on the inspected object and the image based on the diffraction light cannot be obtained from the pattern on the inspected object.

The above relationship can be further described in detail according to the Abbe's diffraction theory. In other words, the Abbe's diffraction theory applies to the relationship between the incident angle ψ to the optical axis of the incident illumination light 30 and the space frequency to be focused.

Whether a grid pattern on the inspected object can be focused depends on whether the first order diffraction light from the grid pattern on the inspected object can pass through the pupil 10a of the imaging system (objective lens 9). If the focusing point remains inside the pupil 10a when a diffraction light 31 is focused onto one point of the pupil 10a of the imaging system (objective lens 9), the diffraction light passes through the imaging system (objective lens 9) and interferes with the 0th order diffraction light on the imaging plane to form the image of the grid pattern. This configuration is advantageous in that a focal depth can be larger.

When the structure of the grid pattern on the inspected object is fine (the pitch P becomes small), the angle θ of the first order diffraction light to the optical axis becomes large and, when the angle θ is larger than NA of the imaging system (objective lens 9), the first order diffraction light cannot pass through the pupil 10a of the imaging system (objective lens 9) and the image of the grid pattern will not be formed.

Although the resolution is improved in a plane between the optical axis and the light source in a simple slanted illumination, the resolution is not improved in other planes. To improve the resolution in an optional direction, it is necessary to apply the annular-looped illumination as described above and prevent an incident illumination light, the first order diffraction light of which is not introduced into NA of the imaging system (objective lens 9) from being introduced in accordance with the direction of the pattern on the inspected object.

A method of illumination in which the 0th order diffraction light does not enter into the pupil 10a of the imaging system (objective lend 9) corresponds to the so-called dark field illumination. If there is only the first order diffraction light in the opening of the imaging system (objective lens 9) with the dark field illumination as described above, the resolution is extremely low.

In FIG. 1, the CPU 20 controls the annular-looped illumination according to the information detected by the image sensor 12b, which serves as a monitor for the pupil 10a of the objective lens 9, by driving the moving mechanism 19 to change over the light source for the annular-looped illumination comprising the disc type mask 5 (secondary light source for annular-looped illumination) so that the first order diffraction light and the 0th order diffraction light always enter into the pupil 10a of the objective lens 9 even when the pattern of the inspected object 1 changes. Specifically, the CPU 20 uses the image of the Fourier transform plane (the surface of the pupil 10a of the objective lens 9) detected by the image sensor 12b and controls the annular-looped illumination to shut off the incident illumination light, a first order diffraction light 23 of which does not enter into the pupil 10a of the objective lens 9, or lowers the intensity of the incident illumination light in accordance with the pattern of the inspected object 1 by driving and controlling the moving mechanism 19 to change over the disc type mask 5 to 5a-1, 5a-2, . . . , or 5b-1, 5b-2, . . .

However, if the periodicity is not observed in the pattern of the inspected object, that is, in a case of a diffraction light (diffraction components are continued) having various diffraction angles in a wide spread, the pattern can be regarded as an isolated pattern (no periodicity is observed) and therefore excessively slanted introduction of the incident illumination light is avoided and the illumination from the secondary light source for an appropriate annular-looped illumination (mask elements 5b-4, 5b-5, 5b-6 and 5b-7 (with small OUT σ) on the disc type mask 5 shown in FIG. 4) or the light source for an ordinary circular illumination (mask elements 5b-8, 5b-9 and 5b-10) is selected.

The edge detector 21 differentiates the image signals of the pattern of the inspected object 1 detected by the image sensor 12a and detects the edge information of the pattern of the inspected object 1 through processing of the threshold value. Accordingly, the CPU 20 calculates the width of the pattern of the inspected object 1 by calculating, for example, an area surrounded by the edge of the pattern according to the edge information of the inspected object 1 detected by the edge detector 21, then calculates the density (pitch P) of the pattern of the inspected object 1 according to the pattern width of this inspected object 1, and controls the annular-looped illumination by driving and controlling the moving mechanism 19 and changing over the light source for the annular-looped illumination which comprises the disc type mask 5 in accordance with the calculated density (pitch P) of the pattern of the inspected object 1. For example, when the density of the pattern is high, the incident illumination light is introduced at a more slanted angle.

Specifically, the CPU 20 compares the density of the pattern of the inspected object 1 to be calculated with a preset value, controls the annular-looped illumination in accordance with the density of the pattern or selects the mask elements 5b-1, 5b-2 and 5b-3 (with a larger OUT σ) shown in FIG. 4 as the light source for the annular-looped illumination so that a slanted incident component is increased as the density of the pattern is higher.

The control of the annular-looped illumination by the CPU 20 can be carried out under a predetermined or preset condition (information as to the type of the pattern of the inspected object 1 to be entered by input unit 32 and mounted on the stage 2 or information as to the type including the process of the inspected object 1 to be obtained from the host computer which controls the manufacturing processes for the inspected object 1 and mounted on the stage 2). In other words, it is necessary to control the annular-looped illumination so as to use the annular-looped illumination available under the preset condition (an annular-looped illumination approximate to a circular illumination (mask elements 5b-4, 5b-5, 5b-6 and 5b-7 (with a smaller OUT σ)) on the disc type mask 5 shown in FIG. 4) or a circular illumination (mask elements 5b-8, 5b-9 and 5b-10 shown in FIG. 4) since the density of the pattern is not so high and the pattern can be identified with a low resolution in a case that the type of the inspected object 1 to be mounted on the stage 2 is, for example, a 4 Mb DRAM memory element, and to use the annular-looped illumination which provides a high resolution under the preset conditions (mask elements 5b-1, 5b-2, and 5b-3 (with a larger OUT a) shown in FIG. 4) since a high density pattern should be detected with the high resolution in a case that the type of the inspected object 1 is the 16 Mb DRAM memory element.

If a mask element with the value a of approximately 0.5 smaller than that of the mask element 5b-10 (σ is 0.65) shown in FIG. 4 is used in the circular illumination, the image sensor 12a receives an image of a deep groove or hole and image signals with high contrast of a pattern including deep grooves or holes can be obtained.

For example, the cell part of the memory element where the pattern density is high can be inspected with the annular-looped illumination which provides a high resolution under the preset condition and broad areas other than the cell part can be inspected with the ordinary circular illumination so that the inspection sensitivity is not deteriorated (so that the intensity of the incident illumination light is not reduced).

Thus, various patterns (circuit patterns) can be detected with high resolution and sensitivity with the objective lens (imaging optical system) 9 by using various modes of annular-looped illuminations including the circular illumination and particularly, the annular-looped illumination can apply to high density patterns on which the degree of integration is increased. The NA of the objective lens (imaging optical system) 9 need not be larger than required so as not to suffice the focal depth.

In a case that the first order diffraction light is prevented from entering into the pupil 10a of the objective lens 9 by, for example, the attenuation filter 38 for partly controlling the light intensity provided at a position 10b conjugated with the pupil 10a of the objective lens 9, the 0th order diffraction light which reaches the attenuation filter 38 through the pupil 10a of the objective lens 9 is shut off or the intensity of this diffraction light is reduced. In a case that the + first order, − first order and 0th order diffraction lights are introduced into the pupil 10a of the objective lens 9, the intensities of the first order and 0th order diffraction lights are controlled to be coincided by, for example, the attenuation filter 38 for partly controlling the light intensity.

The CPU 20 is able to partly control the transmissivity (attenuation ratio) by driving and controlling the moving mechanism 39 and changing over the attenuation filter 38 according to the information detected by the image sensor 12b, which serves a monitor for the pupil 10a of the objective lens 9, to make the image sensor 12a balance and receive the 0th order diffraction light and the first order diffraction light in accordance with the pattern of the inspected object 1.

Figure 6:
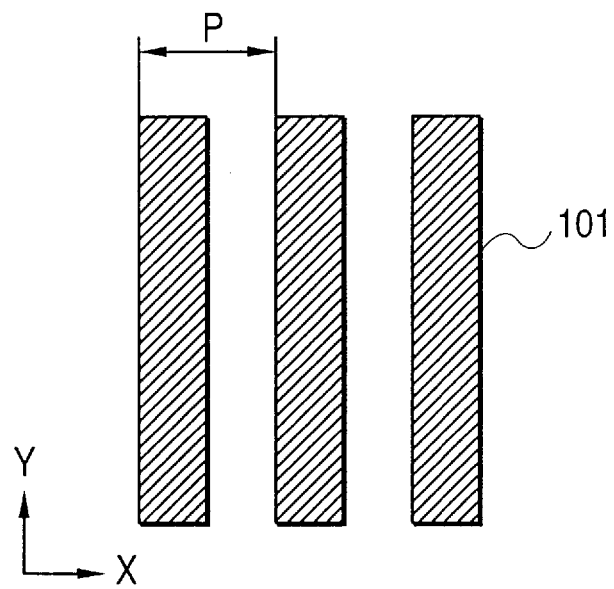
FIG. 6 is an illustration showing a grid pattern to be repeated in the X axis direction which is an embodiment of an LSI wafer pattern.

The detection of the grid pattern in the LSI wafer patterns as shown in FIG. 6 is now described as an example of the inspected object 1 with high resolution by using the annular-looped illumination. FIG. 6 is a schematic diagram showing a grid pattern comprising lines and spaces in a peripheral circuit of the LSI wafer pattern. In FIG. 6, 101 is a pattern line (a wiring pattern including a gate) which extends in the Y axis direction. This grid type pattern line 101 is repeated at the pitch P in the X axis direction. A space (which may be formed with insulation) is formed between the pattern lines 101.

Figure 8:
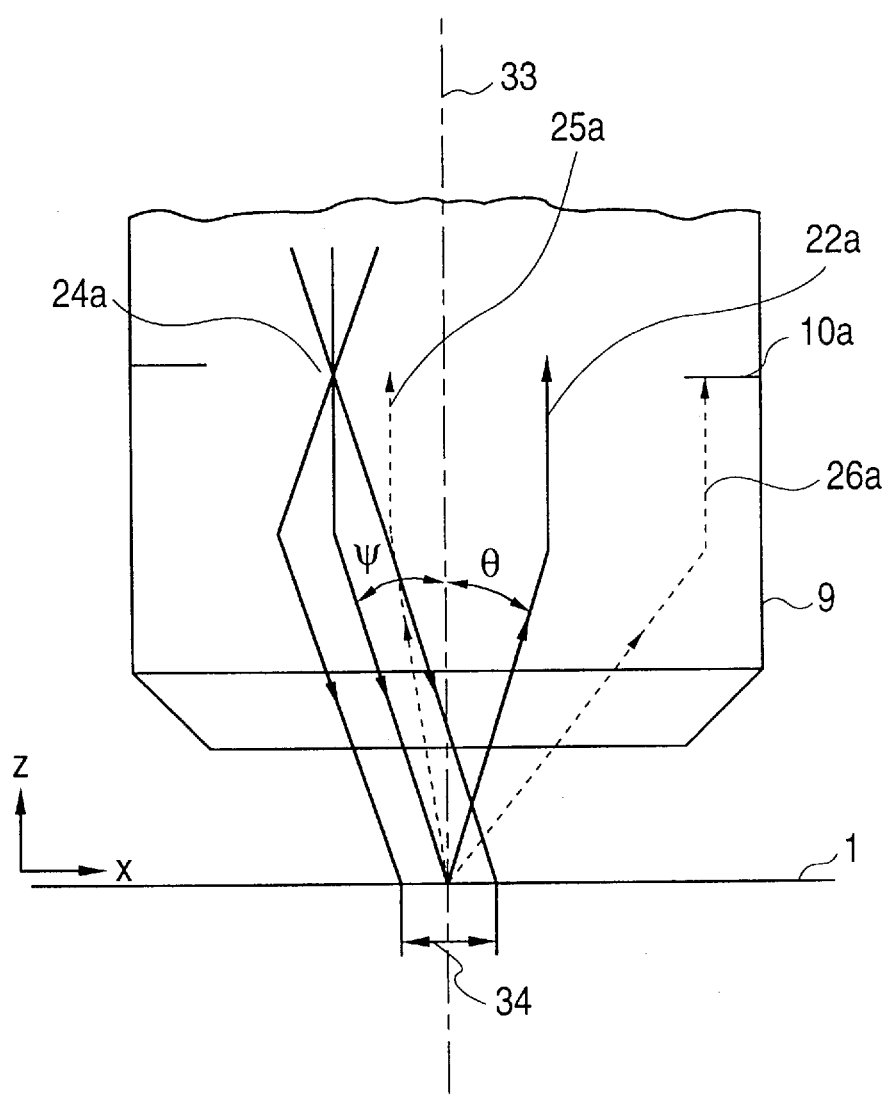
FIG. 8 is an X-Z cross sectional view showing the 0th order diffraction light and the first order diffraction light which are produced from the annular-looped illumination and the grid pattern shown in FIG. 7 to be incident onto the pupil of the objective lens.

FIG. 7 is a schematic illustration showing, on the pupil 10a of the objective lens 9, the incident annular-looped illumination 24 for illuminating the grid pattern shown in FIG. 6, and 0th order diffraction light 22a, + first order diffraction light 25a and − first order diffraction light 26a obtained from reflection of incident illumination light 24a onto the X-Z plane passing through the optical axis 33 from the grid pattern shown in FIG. 6. FIG. 8 is a schematic illustration showing the 0th order diffraction light 22a, the + first order diffraction light 25a and the − first order diffraction light 26a obtained on the X-Z plane passing through the optical axis 33 from reflection of the incident illumination light 24a shown in FIG. 7 from the grid pattern shown in FIG. 6.

As shown in FIGS. 7 and 8, in the pupil 10a of the objective lens 9, the 0th order diffraction light 22a and the + first order diffraction light 25a are observed as having an area and as not being points on an image detected by the image sensor 12b which serves as the monitor for the pupil 10a of the objective lens 9. Reference numeral 34 denotes the range of the annular-looped illumination 24 on the grid pattern of the LSI wafer.

In a case that the grid pattern of the LSI wafer extends in the Y axis direction as shown in FIG. 6, the incident angle $\psi$ of the incident illumination light 24a and the emission angle $\theta$ of the 0th order diffraction light 22a are equal for the relationship represented by the equation 2 described later and the 0th order diffraction light 22a is generated at a position symmetrical to the incident illumination light 24a as shown in FIGS. 7 and 8, and the + first order diffraction light 25a and the − first order diffraction light 26a are generated at left and right positions for the relationship represented by the equation 2. Since the grid pattern of the LSI wafer extends in the Y axis direction, the + first order diffraction light 25a and the − first order diffraction light 26a are generated at left and right positions in the pupil but not generated at upper and lower positions therein and are weak if generated. However, as apparent from FIGS. 7 and 8, not only the 0th order diffraction light 22 but the + first order light 25 or the − first order diffraction light 26 can always be entered into the pupil 10a of the objective lens 9 by using the annular-looped illumination 24, and the image signals of the grid pattern of the LSI wafer can be detected with high resolution by the image sensor 12a.

FIG. 9 is a schematic illustration showing, on the pupil 10a of the objective lens 9, the incident annular-looped illumination 24 for illuminating the grid pattern shown in FIG. 6, and 0th order diffraction light 22b, + first order diffraction light 25b and − first order diffraction light 26b obtained from reflection of incident illumination light 24b onto the Y-Z plane passing through the optical axis 33 from the grid pattern shown in FIG. 6. In other words, since the grid pattern of the LSI wafer extends in the Y axis direction, the incident angle $\psi$ of the incident illumination light 24b and the emission angle $\theta$ of the 0th order diffraction light 22b are equal for the relationship represented by the equation 2 described later and the 0th order diffraction light 22b is generated at a position symmetrical to the incident illumination light 24b, and the + first order diffraction light 25b and the − first order diffraction light 26b are introduced into the pupil 10a of the objective lens 9 as shown in FIG. 9.

However, since the grid pattern of the LSI wafer extends in the Y axis direction, the + first order diffraction light 25b and the − first order diffraction light 26b are weak even though these diffraction lights enter into the pupil 10a of the objective lens 9 and do not therefore make a great contribution to the resolution of the grid pattern of the LSI wafer, and the annular-looped illumination in the Y axis direction can be eliminated by using the mask element 5a-n shown in FIG. 3. Although the first order diffraction light 23b becomes weaker than the 0th order diffraction light 22b, the resolution of the grid pattern of the LSI wafer does not deteriorate considerably even though the 0th order diffraction light 22b is entered into the pupil 10a of the objective lens 9 and received by the image sensor 12a, when both the + first order diffraction light 25b and the − first order diffraction light 26b are entered into the pupil 10a of the objective lens 9 as shown in FIG. 9.

FIG. 10 is a schematic illustration showing, on the pupil 10a of the objective lens 9, incident annular-looped illumination light 24' for illuminating the grid pattern shown in FIG. 6, and 0th order diffraction lights 22a' and 22b', + first order diffraction lights 25a' and 25b' and − first order diffraction lights 26a' and 26b' obtained from reflection of incident illumination lights 24a' and 24b' on the X-Z and Y-Z planes passing through the optical axis 33 from the grid pattern shown in FIG. 6, in a case that OUT σ and IN σ of the annular-looped illumination are respectively made larger than those shown in FIGS. 7 to 9 for the pupil 10a (NA) of the objective lens 9.

In a case that OUT σ and IN σ of the annular-looped illumination are respectively made larger than those shown in FIGS. 7 to 9 for the pupil 10a (NA) of the objective lens 9 as shown in FIG. 10, the + first order diffraction lights 25b' and the − first order diffraction lights 26b' are not entered into the pupil 10a and, when the 0th order diffraction light 22b' is received by the image sensor 12a, the resolution for the grid pattern is deteriorated. Therefore the 0th order diffraction light 22b' faced in the Y axis direction can be prevented from being generated by using the mask element 5a-n shown in FIG. 3 to eliminate the annular-looped illumination in the Y axis direction.

The 0th order diffraction light 22b' can be prevented from being received by the image sensor 12a by providing, for example, attenuation filter 38 for partly controlling the same light intensity as the mask element 5a-n shown in FIG. 3 at a position 10b in conjugation with the position of the pupil 10a of the objective lens 9 and shutting off the 0th order diffraction light 22b' faced to the Y axis direction. The configuration as described above enables detection of the grid pattern with high resolution by the image sensor 12a even with the annular-looped illumination of which OUT σ and IN σ are respectively set to be large for the pupil 10a (NA) of the objective lens 9.

Although, in the embodiment shown in FIG. 10, it is described that OUT σ and IN σ are respectively set to be larger than those shown in FIGS. 7 to 9 for the pupil 10a (NA) of the objective lens 9, also in a case that the pupil 10a (NA) of the objective lens 9 is set to be smaller than that shown in FIGS. 7 to 9 while retaining the sizes of OUT σ and IN σ the same as those in FIG. 7 to 9, a state of generation of the diffraction light entered into the pupil 10a (NA) of the objective lens 9 is as shown in FIG. 10 and it is necessary to prevent the 0th order diffraction light 22b' from being received by the image sensor 12a. In a case that the pitch P of the grid pattern is finer than that shown in FIGS. 7 to 9 and the wavelength λ of the annular-looped illumination light is longer than that shown in FIGS. 7 to 9, generation of the diffraction light entering into the pupil 10a (NA) of the objective lens 9 is as shown in the embodiment in FIG. 10, and it is necessary to prevent the 0th order diffraction light 22b' from being received by the image sensor 12a as known from the relationship represented by the equation 2 described later.

A diffraction phenomenon obtained from the grid pattern with the annular-looped illumination is now described in the relationship between the value σ of an optional annular-looped illumination and the incident angle ψ to the optical axis 33 being described with reference to FIGS. 11 and 12. Specifically, FIG. 11 is an illustration showing the relationship between the value a of the objective lens 9 to the optical axis 33 and the incident angle ψ of the incident illumination light 30 irradiated onto the grid pattern surface of the inspected object 1 and FIG. 12 is an illustration showing the relationship between the incident angle ψ and the emission angle (diffraction angle) θ of the diffraction light 31.

Figure 11:
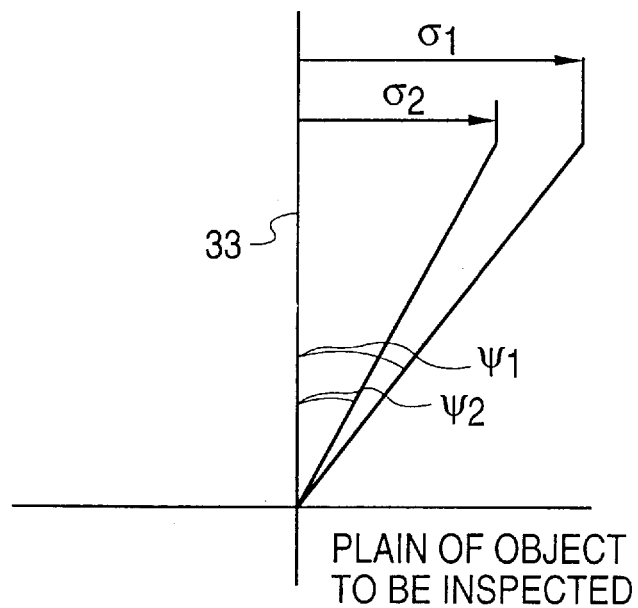
FIG. 11 is an illustration showing the relationship between the value σ and the incident angle ψ of the objective lens.

In FIG. 11, the value σ of the annular-looped illumination light incident into the pupil 10a of the objective lens 9 and the incident angle ψ of the incident illumination light irradiated onto the inspected object 1 are given by the equations shown below:

$$\sigma 1: \sigma 2 = \sin \psi 1: \sin \psi 2$$

$$\sin \psi 2 = (\sigma 2/\sigma 1) \times \sin \psi 1$$

In this examination, the objective lens 9 for which chromatic aberration is compensated and magnification of ×40 and NA=0.8 are given is used.

In this objective lens 9, the maximum incident angle satisfies NA=sin ψmax=0.8 in case of σ=1.0. In otherwords, σ=1.0 indicates NA (opening) (emission pupil) of the objective lens 9.

$$\sin \psi = (\sigma/1) \times 0.8 = 0.8\sigma$$

According to the above relationship, the incident angle ψ can be obtained from the relationship represented by equation 1.

$$\psi = \sin^{-1}(0.8\sigma) \qquad (1)$$

The relationship between the incident angle ψ and the diffraction angle θ is described below.

In FIG. 12, the diffraction angle θ of the m-th order diffraction light 31 has the relationship given by equation 2.

$$P = m\lambda / (\sin \psi - \sin \theta)$$

$$\sin \theta = \sin y - m\lambda/P$$

$$\theta = \mathrm{asin} (\sin \psi - m\lambda/P)) \qquad (2)$$

where λ is a wavelength (μm) of the illumination light, θ is a diffraction angle (emission angle), P is a pattern pitch (μm) and m is s sequential number of the diffraction light. In the equation 2, "asin" denotes "arc sin".

Theoretical values (incident angle ψ and diffraction angle θ) to the value σ of the annular-looped illumination light when the wavelength λ and the pattern pitch P of the inspected object are changed according to the above equations 1 and 2 are given by Tables 2, 3, 4 and 5 below.

TABLE 2

λ = 0.4 μm
P = 0.61 μm (256 Mb)

| σ | 1.00 | 0.90 | 0.80 | 0.70 | 0.60 | 0.50 | 0.40 | 0.30 | 0.20 | 0.10 |
|---|---|---|---|---|---|---|---|---|---|---|
| Incident angle ψ | 53.13 | 46.05 | 39.79 | 34.06 | 28.69 | 23.58 | 18.66 | 13.89 | 9.21 | 4.59 |
| − first order diffraction light | — | — | — | — | — | — | 77.35 | 63.60 | 54.66 | 47.37 |
| + first order diffraction light | 8.29 | 3.68 | −0.90 | −5.40 | −10.13 | −14.83 | −19.62 | −24.57 | −29.72 | −35.15 |

TABLE 3

λ = 0.6 μm
P = 0.61 μm (256 Mb)

| σ | 1.00 | 0.90 | 0.80 | 0.70 | 0.60 | 0.50 | 0.40 | 0.30 | 0.20 | 0.10 |
|---|---|---|---|---|---|---|---|---|---|---|
| Incident angle ψ | 53.13 | 46.05 | 39.79 | 34.06 | 28.69 | 23.58 | 18.66 | 13.89 | 9.21 | 4.59 |
| − first order diffraction light | — | — | — | — | — | — | — | — | — | — |
| + first order diffraction light | −10.58 | −15.28 | −20.10 | −25.06 | −30.24 | −35.70 | −41.58 | −48.04 | −55.45 | −64.64 |

TABLE 4

λ = 0.4 μm
P = 0.7 μm (64 Mb)

| σ | 1.00 | 0.90 | 0.80 | 0.70 | 0.60 | 0.50 | 0.40 | 0.30 | 0.20 | 0.10 |
|---|---|---|---|---|---|---|---|---|---|---|
| Incident angle ψ | 53.13 | 46.05 | 39.79 | 34.06 | 28.69 | 23.58 | 18.66 | 13.89 | 9.21 | 4.59 |
| − first order diffraction light | — | — | — | — | — | — | 77.35 | 63.60 | 54.66 | 47.37 |
| + first order diffraction light | 13.21 | 8.54 | 3.93 | −0.55 | −5.27 | −9.87 | −14.56 | −19.36 | −24.29 | −29.43 |

TABLE 5

λ = 0.4 μm
P = 0.7 μm (64 Mb)

| σ | 1.00 | 0.90 | 0.80 | 0.70 | 0.60 | 0.50 | 0.40 | 0.30 | 0.20 | 0.10 |
|---|---|---|---|---|---|---|---|---|---|---|
| Incident angle ψ | 53.13 | 46.05 | 39.79 | 34.06 | 28.69 | 23.58 | 18.66 | 13.89 | 9.21 | 4.59 |
| − first order diffraction light | — | — | — | — | — | — | — | — | — | 69.58 |
| + first order diffraction light | −3.28 | −7.88 | −12.54 | −17.29 | −22.16 | −27.20 | −32.49 | −38.11 | −44.20 | −51.00 |

Table 2 shows the values in a case that the wavelength λ is 0.4 μm and the pattern pitch P is 0.61 μm, Table 3 shows the values in a case that the wavelength X is 0.6 μm and the pattern pitch P is 0.61 μm, Table 4 shows the values in a case that the wavelength λ is 0.4 μm and the pattern pitch P is 0.7 μm, and Table 5 shows the values in a case that the wavelength λ is 0.6 μm and the pattern pitch P is 0.7 μm, and the incident angle ψ and the diffraction angle θ are calculated according to the above equations 1 and 2. In the LSI wafer pattern, the pattern pitch P=0.61 μm corresponds to 256 Mb and the pattern pitch P=0.7 μm corresponds to 64 Mb. In the above tables, "−" denotes that calculation is impossible (the − first order diffraction light is not theoretically generated). If the diffraction angle θ of the first order diffraction light is 53.13 degrees or over, the first order diffraction light does not enter into the pupil 10a of the objective lens 9 of NA=0.8.

A relationship between the annular-looped illumination (value σ=0.4, 0.6) available with the above theoretical values and the + first order diffraction lights 25 and 25" which are intensified and then obtained from the grid pattern (FIG. 13 shows the pattern pitch P of 0.61 μm and FIG. 14 shows the pattern pitch P of 0.7 μm) is shown in FIGS. 13 and 14 respectively.

FIG. 13 (a) shows the + first order diffraction light 25 which is intensified by the annular-looped illumination 24 of value σ=0.4, 0.6 (wavelength X shall be within the range of 0.4 to 0.6 μm) and obtained from the grid pattern (corresponding to 256 Mb in the LSI wafer pattern) with the pattern pitch P of 0.61 μm, and FIG. 13 (b) is a diagram showing the range of the incident angle ψ of the annular-looped illumination 24 with the value σ of 0.4, 0.6 (wavelength λ shall be within the range of 0.4 to 0.6 μm) and the diffraction angle θ of the + first order diffraction light obtained from the grid pattern (corresponding to 256 Mb in the LSI wafer pattern) with the pattern pitch P of 0.61 μm.

The diffraction range (range of diffraction angle θ) of the + first order diffraction light shown in FIG. 13 (b) corresponds to the annular-looped illumination with the value σ of 0.4, 0.6 in Tables 2 and 3. Intersecting oblique lines in FIG. 13 (b) shows the area of the + first order diffraction light (corresponding to the area of the + first order diffraction light in a case that the average wavelength (wavelength λ is 0.5 μm) of the annular-looped illumination light) which is obtained from the grid pattern with the pattern pitch P of 0.61 μm by being intensified with the annular-looped illumination with the value σ of 0.4, 0.6. In other words, FIG. 13 (a) shows an annular-looped area 25 of the + first order diffraction light which is intensified and obtained from the grid pattern with the pattern pitch P of 0.61 μm and entered onto the pupil 10a of the objective lens 9.

Figure 14A:
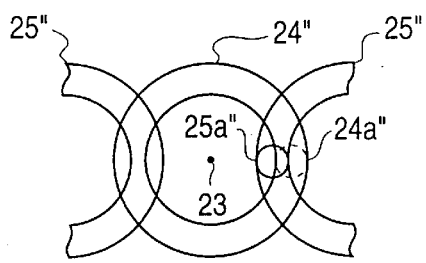
FIGS. 14(a) and 14(b) are illustrations a linear diagram showing a situation where + first order diffraction light is produced when the annular-looped illumination with the wavelength of λ=0.4 to 0.6 μm and the value σ of 0.60 to 0.40 is cast to a grid pattern of P=0.7 μm.
Figure 14B:
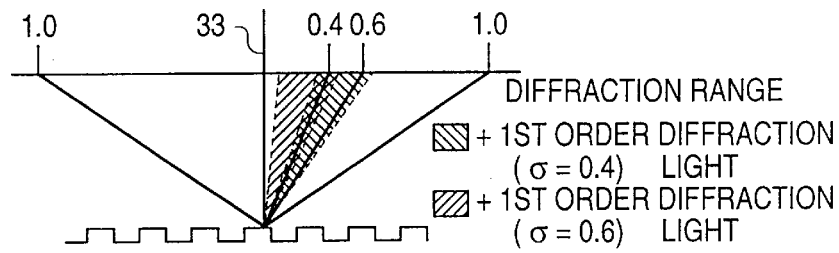

FIG. 14(a) shows the + first order diffraction light 25" which is intensified by the annular-looped illumination 24 with the value σ of 0.4, 0.6 (wavelength λ shall be within the range of 0.4 to 0.6 μm) and obtained from the grid pattern (corresponding to 64 Mb in the LSI wafer pattern) with the pattern pitch P of 0.7 μm, and FIG. 14(b) is a diagram showing the range of the incident angle ψ of the annular-looped illumination 24 with the value σ of 0.4, 0.6 (wavelength λ shall be within the range of 0.4 to 0.6 μm) and the diffraction angle θ of the + first order diffraction light obtained from the grid pattern (corresponding to 64 Mb in the LSI wafer pattern) with the pattern pitch P of 0.7 μm.

The diffraction range (range of diffraction angle θ) of the + first order diffraction light shown in FIG. 14(b) corresponds to the annular-looped illumination with the value σ of 0.4, 0.6 in Tables 4 and 5. Intersecting oblique lines in FIG. 14(b) shows the area of the + first order diffraction light (corresponding to the area of the + first order diffraction light in a case that the average wavelength (wavelength λ is 0.5 μm) of the annular-looped illumination light) which is obtained from the grid pattern with the pattern pitch P of 0.7 μm by being intensified with the annular-looped illumination with the value σ of 0.4, 0.6. In other words, FIG. 14(a) shows an annular-looped area 25" of the + first order diffraction light which is intensified and obtained from the grid pattern with the pattern pitch P of 0.7 μm and entered onto the pupil 10a of the objective lens 9.

From comparison of FIGS. 13 and 14, it is apparent that, if the pattern pitch P is smaller, the diffraction angle θ of the first order diffraction light becomes large and therefore the annular-looped illumination is required.

Thus, the annular-looped illumination with the value σ of 0.4, 0.6 as shown in FIGS. 13 and 14 can be materialized by using the mask element 5b-6 shown in FIG. 4.

The above description is based on the equations 1 and 2 shown above. In an experiment conducted by the present inventors, substantially the same results were obtained (the result shown in FIG. 13: the grid pattern with the pattern pitch P of 0.61 μm (corresponding to 256 Mb in the LSI wafer pattern); the result shown in FIG. 14: the grid pattern with the pattern pitch P of 0.7 μm) (corresponding to 64 Mb in the LSI wafer pattern).

In the above-described embodiments shown in FIGS. 7 to 14, the grid patterns which are repeated in the X axis direction in the LSI wafer pattern as shown in FIG. 6 have been described. Actually, in the LSI wafer pattern, there is a grid pattern comprising pattern lines 102 to be repeated in the Y axis direction as shown in FIG. 15.

Figure 15:
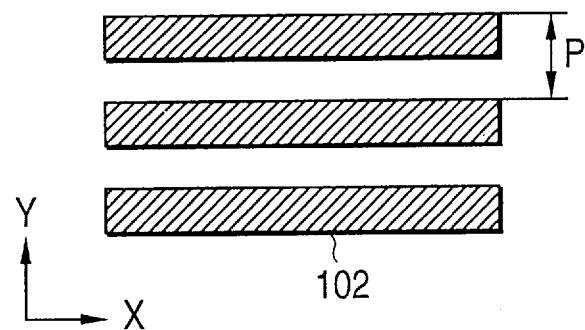
FIG. 15 is an illustration showing a grid pattern to be repeated in the Y axis direction which is an embodiment of the LSI wafer pattern.
Figure 16:
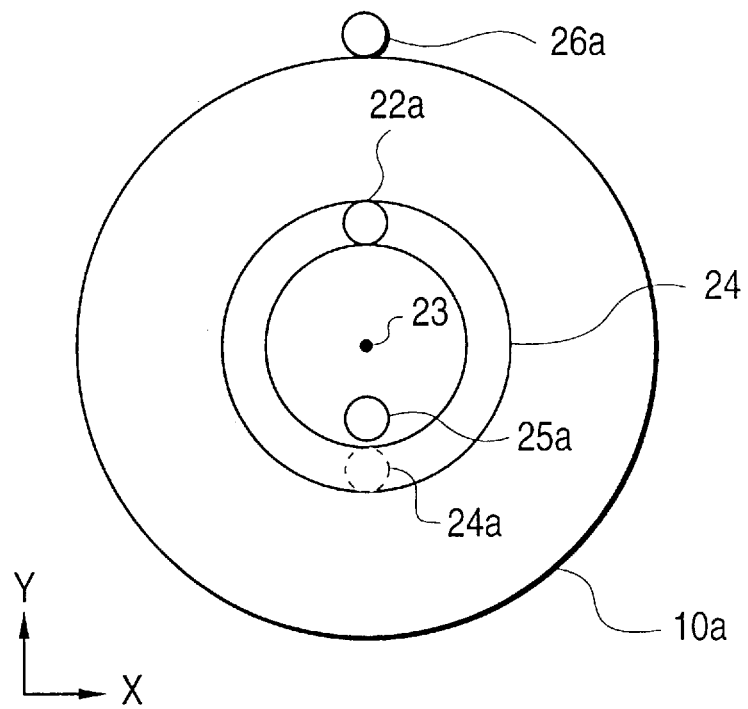
FIG. 16 is an X-Y plan view on the pupil of the objective lens, showing 0th order diffraction light and first order diffraction light which are produced in the Y axis direction from the grid pattern shown in FIG. 15 by casting the annular-looped illumination onto the grid pattern to be incident onto the pupil of the objective lens.

The diffraction lights 22a, 25a and 26a obtained from the grid pattern comprising pattern lines 102 repeated in the Y axis direction as shown in FIG. 15 with the annular-looped illumination 24 are entered into the pupil 10a of the objective lens 9 as shown in FIG. 16. The grid pattern comprising pattern lines 101 shown in FIG. 6 and the grid pattern comprising pattern lines 102 shown in FIG. 15 are shifted by 90 degrees from each other and therefore the state shown in FIG. 16 is obtained by rotating the state shown in FIG. 7 by 90 degrees.

Accordingly, the state of generation of the diffraction light obtained from the grid pattern comprising the pattern lines 102 shown in FIG. 15 is the same as obtained by rotating the state of generation of the diffraction light shown in FIGS. 8 to 10 by 90 degrees. In other words, it is apparent that the 0th order diffraction light 22a, + first order diffraction light 25a and − first order diffraction light 26a obtained reflected at the grid pattern shown in FIG. 15 from the incident illumination light 24a entered into the Y-Z plane passing through the optical axis 33 of the incident annular-looped illumination light 24, are made incident onto the pupil 10a of the objective lens 9 as shown in FIG. 16 and the incident illumination light 24a in a direction intersecting the pattern lines 102 is effective for improvement of the resolution.

However, even though the + first order diffraction light 25b and the − first order diffraction light 26b, which are obtained from reflection of the incident illumination light, which is made incident into the X-Z plane passing through the optical axis 33, of the incident annular-looped illumination light 24 from the grid pattern shown in FIG. 15, are introduced into the pupil 10a of the objective lens 9 as described in FIG. 9, such diffraction lights are weaker than the 0th order diffraction light 22b and do not contribute to improvement of the resolution and therefore it is preferable to eliminate the incident illumination light to be made incident in the X axis direction (X-Z plane passing through the optical axis 33) of the incident annular-looped illumination light 24 by using the mask element 5a-m shown in FIG. 3.

In any event, the CPU 20 can detect the distribution of the incident diffraction light which is produced from the grid pattern and entered into the pupil 10a of the objective lens 9 by the annular-looped illumination, according to the image signals obtained from the image sensor 12b which receives the image (the producing position and brightness of the 0th order diffraction light 22a and the producing position and brightness of the + first order diffraction light 25a) on the pupil 10a (Fourier transform plane) of the objective lens 9.

In other words, the CPU 20 can select the mask element by driving and controlling the moving mechanism 19 in accordance with the distribution (the producing position and brightness of the 0th order diffraction light and the producing position and brightness of the + first order diffraction light 25a) of the diffraction light to be entered into the pupil 10a of the objective lens 9 detected according to the image signals to be obtained from the image sensor 12b, and can obtain an annular-looped illumination suitable for the grid pattern (LSI wafer pattern) of the inspected object 1. Consequently, high resolution image signals of the grid pattern (LSI wafer pattern) of the inspected object 1 can be obtained from the image sensor 12a.

The following describes the operation of a device as represented, for example, by the attenuation filter 38 for partly controlling the intensity of light which is provided at a position 10b in conjunction with the position of the pupil 10a of the objective lens 9. Specifically, as shown in FIGS. 9 and 10, the 0th order diffraction light 22b, 22b' which need not be entered into the pupil 10a of the objective lens 9 and received by the image sensor 12a can be shut off by the attenuation filter 38. In this case, the attenuation filter 38 serves as a space filter.

Figure 17:
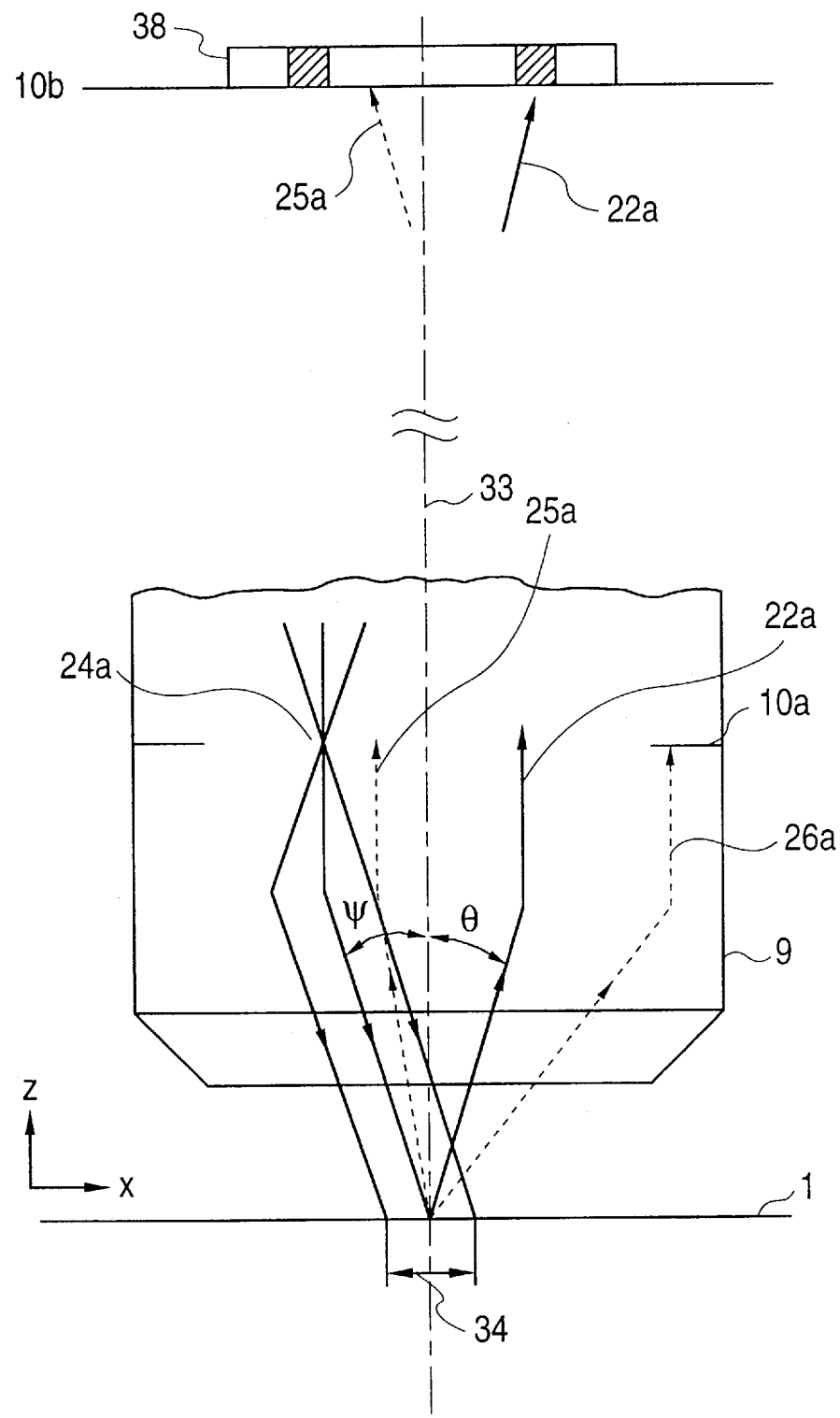
FIG. 17 is an Y-Z cross sectional view showing a state of attenuation of 0th order diffraction light through an attenuation filter (light quantity control filter)
Figure 18:
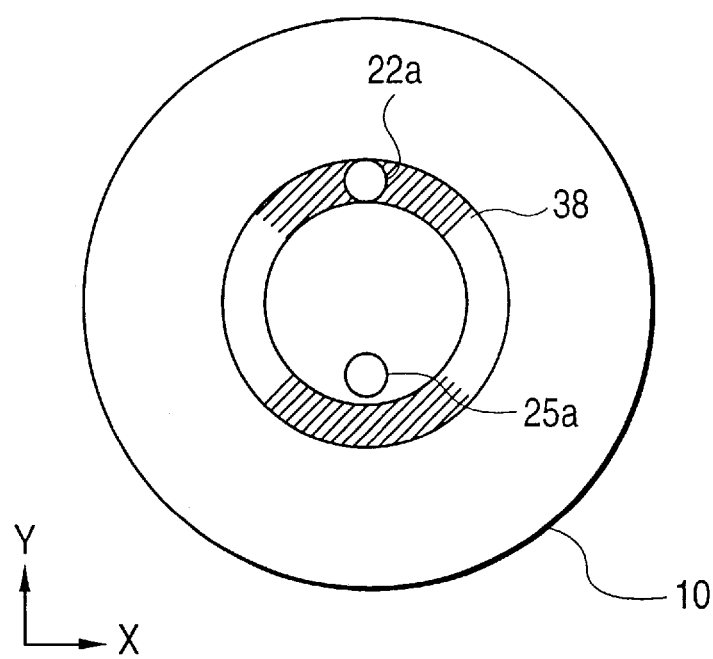
FIG. 18 is an X-Y plan view on the pupil conjugated with the pupil of the objective lens showing a state of attenuation of the 0th order diffraction light through the attenuation filter (light quantity control filter) for which the contents shown in FIG. 17 are provided at a position conjugated with the pupil of the objective lens.

By controlling the intensity of the 0th order diffraction light 22a entered into the pupil 10a of the objective lens 9 as shown in FIGS. 8 and 16 by the attenuation filter 38 provided at the position 10b in conjunction with the position of the pupil 10a of the objective lens 9 as shown in FIGS. 17 and 18, the image sensor 12a is able to balance the intensity of the 0th order diffraction light 22a and the intensity of the + first order diffraction light 25a which are entered into the pupil 10a of the objective lens 9 and receive these diffraction lights and consequently, the image of the grid pattern of the inspected object 1 can be detected with high resolution and high contrast. The above-described attenuation filter 38 has a shape identical to the mask element shown in FIG. 3. However, as shown in FIG. 3, the attenuation filter 38 need not have a ring type shape and can be shaped as desired if it is able to control the light intensity at a desired position. However, if a ring-shaped attenuation filter 38 is used, it is necessary to optimize the annular-looped illumination 24 so that the 0th order diffraction light 22a and the + first order diffraction light 25a are not generated in the same ring-shaped area.

FIG. 17 is a diagram showing that the 0th order diffraction light 22a and the + first order diffraction light 25a generated from the grid pattern of the inspected object 1 by the annular-looped illumination 24a reaches the pupil 10a of the objective lens 9 and the pupil 10b at a position in conjugation with the pupil 10a. FIG. 18 is a diagram showing the attenuation filter 38 disposed on the pupil 10b. In other words, it is known that, of the 0th order diffraction light 22a and the + first order diffraction light 25a which are introduced into the pupil 10a of the objective lens 9, the intensity of the 0th order diffraction light 22a is controlled on the pupil 10a by the attenuation filter 38.

Figure 19A:
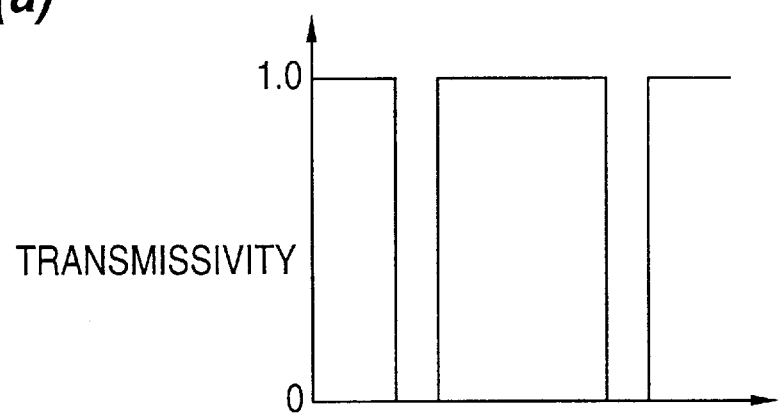
FIG. 19 is an illustration showing a cross sectional shape of the attenuation filter (light quantity control filter) and its transmissivity characteristic when the transmissivity is set to be approximately 0.
Figure 19B:
Figure 20A:
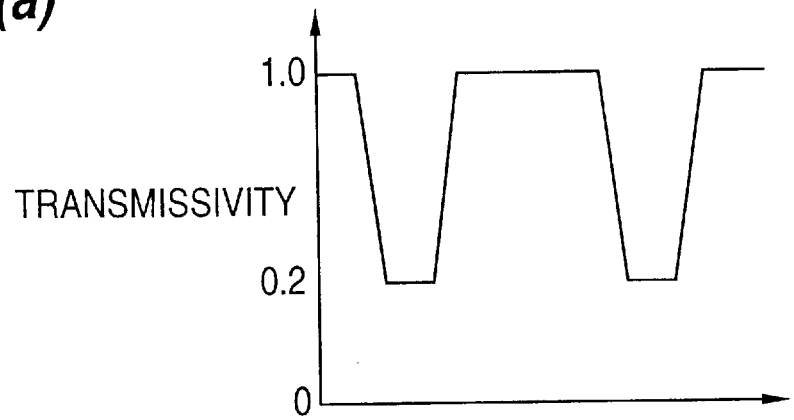
FIGS. 20a and 20b show an illustration showing a cross sectional shape of the attenuation filter (light quantity control filter) and its transmissivity characteristic when the transmissivity is set to be approximately 0.2.
Figure 20B:

FIG. 19(a) is a schematic diagram of an attenuation filter 38a showing the transmission characteristic of the attenuation filter 38a and FIG. 19(b) shows a graphical shape thereof. FIG. 20(a) shows another attenuation filter 38b and the transmission characteristic thereof and FIG. 20(b) shows a graphical shape thereof. The transmission characteristic of the attenuation filter 38 and the graphical shape thereof can be optimized in compliance with the 0th order diffraction light 22a and the + first order diffraction light 25a which are produced from the grid pattern of the inspected object 1 by the annular-looped illumination 24a.

If the annular-looped illumination can be optimized in accordance with the grid pattern (LSI wafer pattern) of the inspected object 1, the attenuation filter 38 need not be provided. However, for optimization only with the annular-looped illumination, it is necessary to prepare and select various types of annular-looped illuminations to meet various types of patterns on the inspected object 1. For minimizing the scope of selection of the annular-looped illumination, it is preferable to control the intensities of the diffraction lights by using the attenuation filter 38 at the light receiving side and detect the image of the grid pattern of the inspected object 1 in high resolution and contrast by the image sensor 12a.

The CPU 20 can select the attenuation filter 38 by driving and controlling the moving mechanism 39 in accordance with the distributions of the diffraction lights (the producing position and brightness of the 0th order diffraction light 22a and the producing position and brightness of the + first order diffraction light 25a) which are detected according to the image signals obtained from the image sensor 12b and entered into the pupil 10a of the objective lens 9, and can obtain the intensities of the 0th order diffraction light and the + first order diffraction light suited to the grid pattern (LSI wafer pattern) of the inspected object 1. Consequently, high resolution image signals of the grid pattern (LSI wafer pattern) of the inspected object 1 can be obtained from the image sensor 12a.

Since it is difficult to implement optimization only with the annular-looped illumination to meet various patterns on the inspected object 1, it is necessary to control the intensities of the diffraction lights received by the image sensor 12a through the attenuation filter 38 as described above, and the detection sensitivity by controlling the threshold values in image processing to be carried out by the comparator circuit 17 or the CPU 20. The control of the threshold values in image processing to be carried out by the comparator circuit 17 or the CPU 20 can be carried out according to the image on the pupil 10b of the objective lens 9 to be detected by the image sensor 12b or the image of the pattern on the inspected object 1 to be detected by the image sensor 12a.

The CPU 20 can be adapted to determine an area having a pattern with high repeatability such as, for example, a memory cell in accordance with a locality distribution (the producing position and the intensity including the spread) of the diffraction light in the image (image on the pupil 10b of the objective lens 9) on the Fourier transform plane to be detected by the image sensor 12b, and to control the threshold values in image processing to be carried out by the comparator circuit 17 or the CPU 20, to raise the detection sensitivity. On the contrary, in a case that the CPU 20 determines an area having a pattern with a lower repeatability, the detection sensitivity can be lowered by controlling the threshold values in image processing to be carried out by the comparator circuit 17 or the CPU 20.

Particularly, for inspecting a defect of a pattern on the inspected object 1 in image processing to be carried out by the comparator circuit 17 or the CPU 20, a defect in an area including a pattern having high repeatability such as, for example, a memory cell can be easily detected with the annular-looped illumination, by controlling the threshold values to increase the detection sensitivity in accordance with the locality distribution (the producing position and the intensity including the spread) of the diffraction light in the image (the image on the pupil 10b of the objective lens 9) on the Fourier transform plane to be detected by the image sensor 12b.

Figure 21:
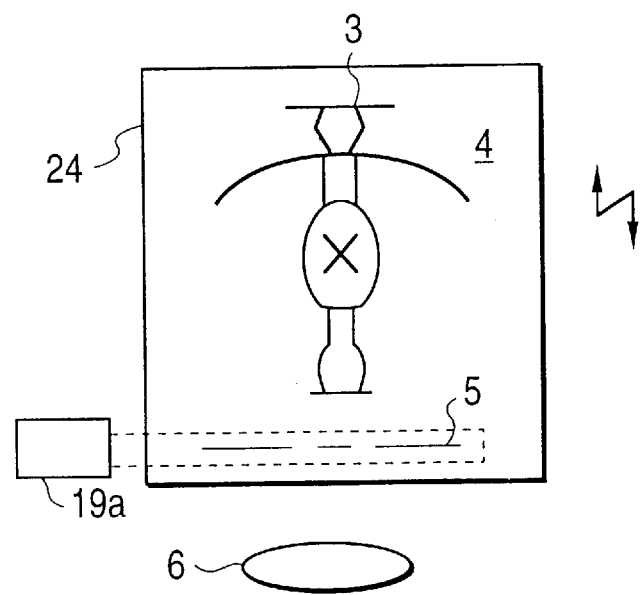
FIG. 21 is a diagram showing an embodiment in which a light house is controlled in the optical axis direction for a collimator lens in the annular-looped illumination according to the present invention.
Figure 22:
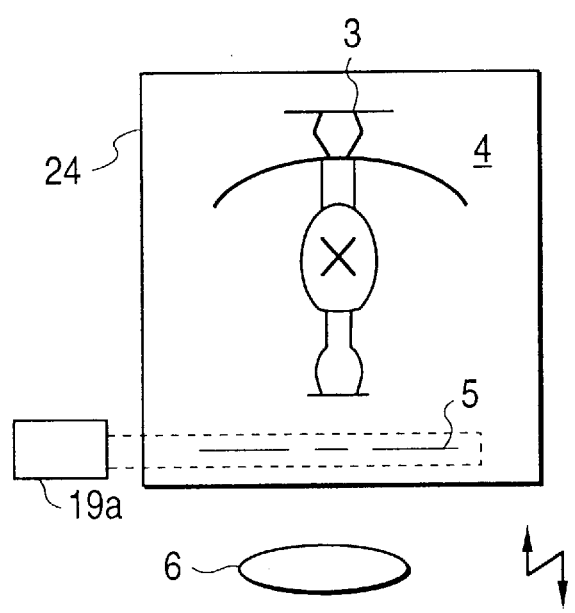
FIG. 22 is a diagram showing an embodiment in which a collimator lens is controlled in the optical axis direction for a light house lens in the annular-looped illumination according to the present invention.

Another embodiment in which the shape of the ring of the annular-looped illumination to be emitted from the disc type mask (secondary light source for annular-looped illumination) formed with a plurality of virtual spot light sources is changed is described with reference to FIGS. 21 and 22. In other words, FIGS. 21 and 22 show other embodiments for controlling various annular-looped illuminations. In FIG. 21, the shape of the ring is changed and the annular-looped illumination is controlled by moving the light house 124 comprising the Xe lamp 3, the elliptic mirror 4 and the disc type mask 5 for forming the annular-looped illumination towards the collimator lens 6 in the optical axis direction. In FIG. 22, the shape of the ring is changed and the annular-looped illumination is controlled by moving the collimator lens 6 toward the light house 124 comprising the Xe lamp 3, the elliptic mirror 4 and the disc type mask 5 for forming the annular-looped illumination in the optical axis direction.

In an embodiment of the light house 124 which forms the secondary light source 5 for the annular-looped illumination formed with a plurality of virtual spot light sources shown in FIGS. 1, 21 and 22, an arrangement of the Xe lamp 3 in the vertical direction is shown. When the Xe lamp 3 is arranged in the vertical direction, the light flux in the optical axis direction reduces and therefore the Xe lamp can be arranged in the horizontal direction to increase the light flux in the optical axis direction. Not only the Xe lamp but also a Hg lamp and a halogen lamp can be used as the light source in the light house 124.

In a case that the disc type mask 5 (secondary light source for annular-looped illumination) formed with a plurality of virtual spot light sources is selected in accordance with the pattern of the inspected object 1, the light quantity of the annular-looped illumination emitted from the secondary light source 5 for the annular-looped illumination substantially varies and the CPU 20 controls the light quantity by controlling the light quantity adjusting filter 14 such as an ND filter in accordance with an image signal 41 obtained from the image sensor 12a through the A/D converter 19.

A microscope system (microscopic observation system) to be used in inspection of a pattern of an inspected object 1 using an annular-looped illumination according to the present invention is described with reference to FIG. 23 which shows a microscope system (microscopic observation system) according to a second embodiment of the present invention applied to the inspection of the pattern of the inspected object 1 such as an LSI wafer pattern (microscopic observation system) according to the second embodiment of the present invention.

The microscope system using the annular-looped illumination formed with a plurality of virtual spot light sources is described only with respect to its characteristic parts with omission of the description of the parts common to the pattern inspection apparatus shown in FIG. 1. In FIG. 23, members 12a' and 12b' represent TV cameras which are used as the image sensors 12a and 12b shown in FIG. 1 and the operator can visually observe the output images from the TV cameras on monitors 27a and 27b. Members 12a' and 12b' can be used if they can detect the image, and can therefore be formed with image sensors and not the TV cameras.

In other words, the TV camera 12a' detects a pattern image and the TV camera 12b' detects an image on a pupil 10a of an objective lens 9, and these images are displayed on the monitors 27a and 27b. A controller 46 is connected to a specimen stage 2 so as to be driven and controlled for movement in X, Y, Z and θ (rotation) axis directions by a driver 45. This controller 46 drives and controls the moving mechanism 19, the light house 124, and the collimator lens 6 in accordance with an image with a locality distribution of the first order diffraction light including the 0th order diffraction light which are introduced into the pupil 10*a* of the objective lens 9 and detected by the TV camera 12*b'* and displayed on the monitor 27*b,* and selects the annular-looped illumination or a normal circular illumination suited for the pattern of the inspected object 1. For driving and controlling the disc type mask 5 by the moving mechanism 19, a mask element formed on the disc type mask 5 can be selected. For driving and controlling the light house 124 and the collimator lens 6, these can be driven and controlled relatively in the arrow direction as shown in FIGS. 21 and 22.

The controller 46 drives and controls the moving mechanism 39 and selects an attenuation filter 38 suited for the pattern of the inspected object 1 according to an image of a locality distribution of the first order diffraction light including the 0th order diffraction light which are entered into the pupil 10*a* of the objective lens 9 and detected by the TV camera 12*b'* displayed on the monitor 27*b*. If a circular illumination suitable or normal for the pattern of the inspected object 1 can be selected with the secondary light source 5 for the annular-looped illumination, the attenuation filter 38 need not always be provided.

The controller 46 controls the light quantity control filter 14 to obtain an appropriate quantity of light from the pattern of the inspected object 1 by driving and controlling a control mechanism 14*b* according to an image of the pattern of the inspected object 1 which is detected by the TV camera 12*a'* and displayed on the monitor 27*a.*

A microscopic observation system thus using the annular-looped illumination enables to observe a high density pattern with high resolution and contrast according to the image of the pattern of the inspected object 1, which is detected by the TV camera 12*a'* and displayed on the monitor 27*a,* even though the pitch P (for example, 0.7 $\mu$m or 0.61 $\mu$m) of the grid pattern such as memory devices as 64 Mb DRAM and 256 Mb DRAM as on the LSI wafer pattern is close to wavelength $\lambda$ (for example, 400 to 600 nm) of the illumination light to result in the high density.

When a mask element with the value a of approximately 0.5 is used for illumination in the annular-looped illumination, an image of deep groove or hole can be received by the TV camera 12*a'* and displayed with high contrast on the monitor 27*a*.

Modifications of the above-described first and second embodiments as a third embodiment are now described. The above-described first and second embodiments have been described with respect to the annular-looped illumination and the circular illumination. The above-described annular-looped illumination includes a modified illumination (slanted illumination) (This modified illumination is based on the illuminating condition under which at least the 0th order diffraction light and the first order or second order diffraction light are introduced into the pupil 10*a* of the objective lens 9.). The dark field illumination is not included in the modified illumination (slanted illumination) since the 0th order diffraction light thereof is not generally entered into the pupil 10*a* of the objective lens 9.

In the first and second embodiments, the transmissivity of light is attenuated by the attenuation filter 38 as shown in FIGS. 19 and 20. However, the light quantity of the 0th order diffraction light 22*a* can be attenuated as compared with the + first order diffraction light 25*a* received by the image sensor 12*a* by a phase shifting method, that is, a method for shifting the phase of the 0th order diffraction light 22*a* by using a phase film. In other words, although a device such as the attenuation filter 38 for partly controlling the light intensity is provided at a position 10*b* in conjugation with the position of the pupil 10*a* of the objective lens 9 in the first and second embodiments, a phase plate can be provided at this position 10*b*. For example, the intensity of the 0th order diffraction light 22*a* received by the image sensor 12*b* can be attenuated by advancing the phase of the 0th order diffraction light 22*a* as much as $\pi/2$ with reference to the phase of the + first order diffraction light 25*a*. In addition, the intensity of the 0th order diffraction light 22*a* to be received by the image sensor 12*b* can be attenuated by providing the phase plate with an absorption characteristic.

Although, in the first and second embodiments, the 0th order diffraction light and + first order diffraction lights are described in a combination framework, it is apparent that these embodiments can apply to the framework of the 0th order diffraction light (non-diffraction light) and the diffraction light ($\pm$ first order diffraction lights and $\pm$ second order diffraction lights). In other words, the annular-looped illumination can be used so that the 0th order diffraction light and the + second order diffraction light or the − second order diffraction light obtained from the pattern are made incident into the pupil 10*a* of the objective lens 9, even though the pitch P of the pattern becomes finer (the pattern has a higher density). Generally, the first order diffraction angle is smaller than the second order diffraction angle as given in the relationship represented by the equation 2. However, in some cases, the second order diffraction angle may be smaller than the first order diffraction angle depending on the pitch P of the pattern and the wavelength $\lambda$ of the annular-looped illumination.

In the first and second embodiments, for example, the Xe lamp 3 (the dimensions are not shown) is used as the light source in the light house 124 but a large light source (a light source which irradiates an incoherent light) or a spot light source (a light source which irradiates a coherent light) can be used. An appropriate value a can be obtained only with the primary light source (without a mask element) by selecting the light source.

Although the first and second embodiments are described with a common wavelength of 400 to 600 nm as the wavelength $\lambda$ of the annular-looped illumination, the illumination wavelength is not described. A wavelength of the so-called i ray (approximately 365 nm) or a short wavelength of an excimer laser beam (ultraviolet ray) can be used as the wavelength $\lambda$ of the annular-looped illumination. It is apparent that the resolution can be further improved if a light of short wavelength such as the excimer laser beam (ultraviolet ray) is used.

The control of the annular-looped illumination in the first and second embodiments can be carried out for each type of pattern of the inspected object (for example, in case of the LSI wafer pattern, each process or each type of the LSI wafer). The annular-looped illumination can be dynamically controlled in one LSI wafer. In case of inspecting a defect of the pattern of the inspected object 1, the sensitivity can be controlled for each type of pattern of the inspected object as in the control of the annular-looped illumination or can be dynamically controlled in one LSI wafer.

The secondary light source for the annular-looped illumination, including the primary light source (Xe lamp 3) for use in the light house 124 in the first and second embodiments can be adjusted by using a mirror surface wafer as the inspected object 1 so that a ring type intensity distribution (a distribution of a ring-shaped 0th order diffraction light 22 on the pupil 10*a* of the objective lens 9 to be detected by the image sensor 12*b*) becomes uniform. In other words, the secondary light source for the annular-looped illumination can be adjusted by adjusting, for example, the positions of the Xe lamp 3 and an elliptic mirror 4 which forms the secondary light source for the annular-looped illumination so that the distribution of the ring-shaped 0th order diffraction light 22 on the pupil 10a of the objective lens 9 detected by the image sensor 12b using the mirror surface wafer as the inspected object 1.

In the first and second embodiments, it is described that the image information (monitor information) based on the locality distribution (position and brightness, including the spread) of the diffraction lights (0th order diffraction light and + first order diffraction light) on the pupil 10a of the objective lens 9 detected by the image sensors 12b and 12b' is used to control various parts by the CPU 20 or the controller 46. In other words, the control of the conditions for various parts includes the control of illumination conditions such as control of the annular-looped illumination (for example, control of IN σ and OUT σ and the incident range shown in FIGS. 3 and 4) and the light quantity control by means of the light quantity control filter 14, the control of the light quantity detected by the attenuation filter 38, and the control of detection sensitivity in the comparator circuit 17. The CPU 20 or the controller 46 determines whether the image information based on the locality distribution of the diffraction lights on the pupil 10a of the objective lens 9 detected by the image sensors 12b and 12b' is obtained, for example, from the repeated portion or the other area of the memory device and consequently, can controls the annular-looped illumination including an appropriate circular illumination in accordance with whether the identified repeated portion or the other portion.

Figure 25:
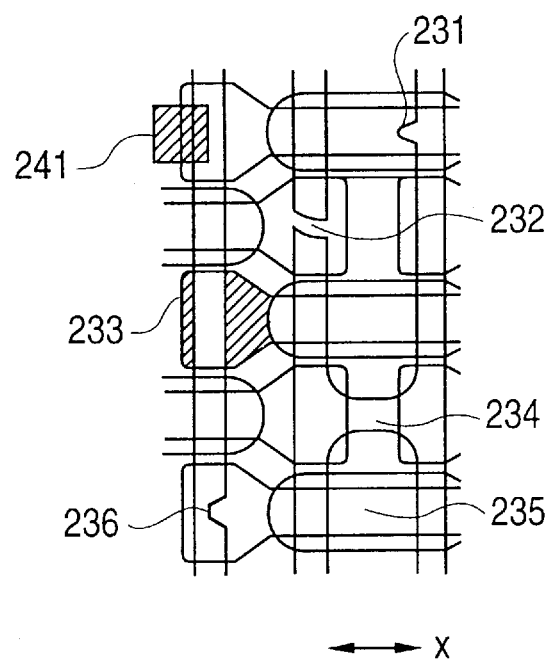
FIG. 25 is an illustration showing the relation to the dimensions of the pixel to be detected at a portion on the wafer pattern shown in FIG. 24.
Figure 26A:
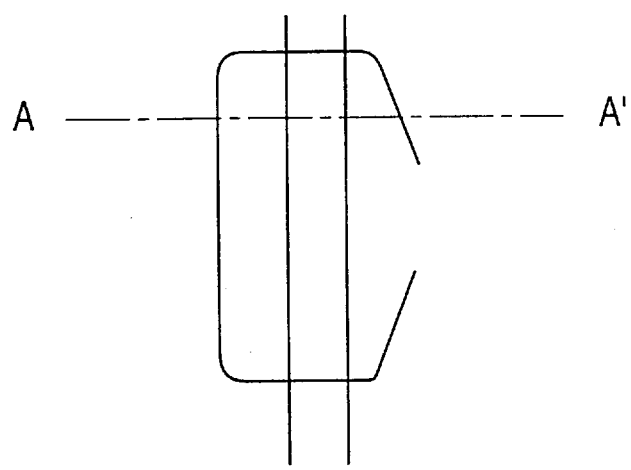
FIGS. 26(a) and 26(b) show the pattern at the portion shown in FIG. 25 and an image signal waveform corresponding to the brightness which faithfully represents this pattern.
Figure 26B:
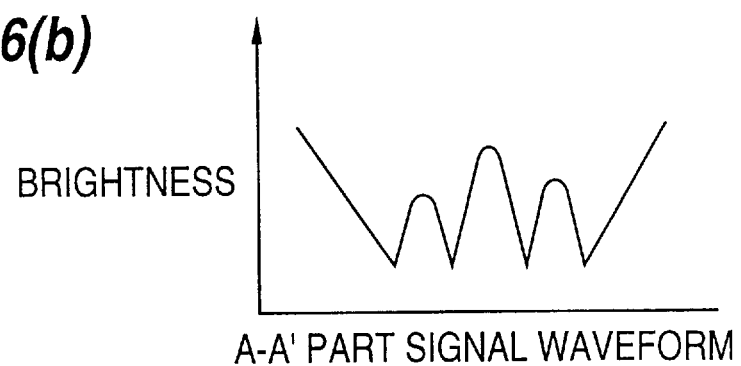
Figure 27A:
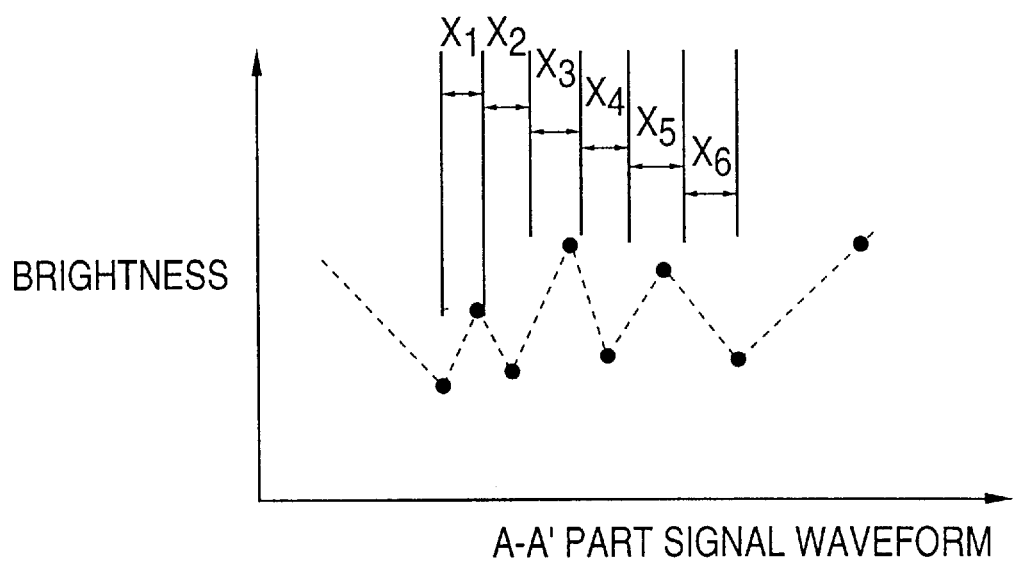
FIGS. 27(a) and 27(b) show an image signal corresponding to a sampled brightness obtained by sampling image signals corresponding to the brightness shown in FIG. 26.
Figure 27B:
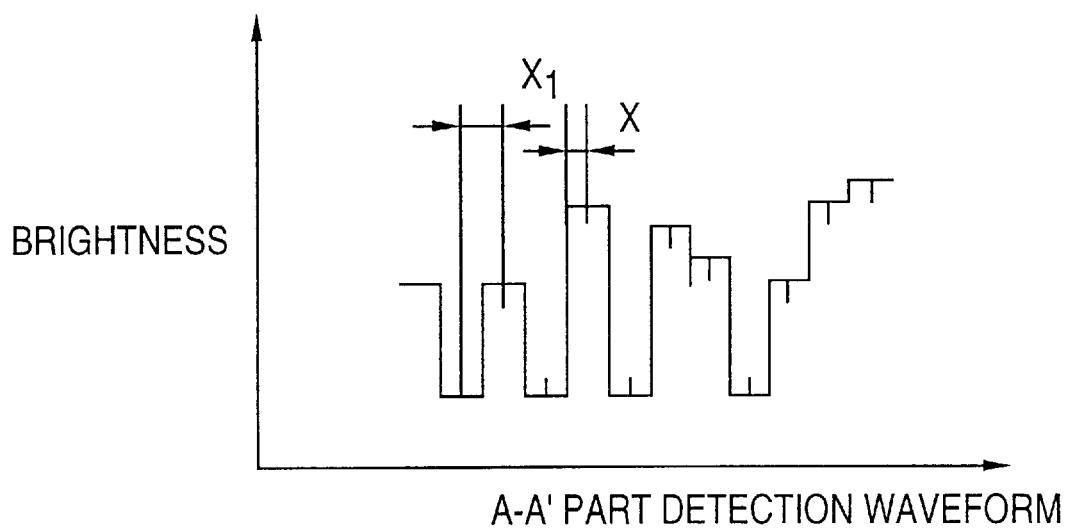

A fourth embodiment of the present invention for inspecting a defect of a memory cell part of an LSI wafer pattern by using an annular-looped illumination to improve the optical resolution is described with reference to FIGS. 24 to 27. FIG. 24 shows a defect of the memory cell part of the LSI wafer pattern. FIG. 25 shows the relationship between the LSI wafer pattern and the detection pixel obtained from an A/D converter 15a. FIGS. 26(a) and 26(b) show a pattern and a waveform of an image signal received with high resolution from a high density pattern by the image sensor 12a with the annular-looped illumination and obtained from the image sensor 12a. FIGS. 27(a) and 27(b) explain sampling of image signals shown in FIG. 26 to be carried out by the A/D converter 15a.

There are various defects (for example, a projection 231, an opening 232, a discoloration 233, a short-circuiting 234, a chipping 235, and a stain 236) on the memory cell part of the LSI wafer pattern as shown in FIG. 24 and therefore, for detecting these defects with high reliability, the inspection apparatus should be able to detect the LSI wafer pattern as image signals with high resolution by the image sensor 12a. High resolution image signals shown in FIG. 26(b) are obtained from the pattern shown in FIG. 26(a) by using the annular-looped illumination. FIG. 26(a) shows a partly extended view of the pattern shown in FIG. 24 and FIG. 26(b) shows the waveform indicating the position of the pattern A—A' on the horizontal axis and the brightness of the image signal (pattern detection signal) obtained from the image sensor on the vertical axis. In FIG. 26(a), it is shown that high resolution image signals representing the edge information of the pattern are obtained from the image sensor 12a by using the annular-looped illumination.

When the annular-looped illumination is used, the + first order diffraction light with various diffraction angles and a spread (dull spread) is obtained from the defects such as the projection 231, the chipping 236 and the stain 235 and image signals differing from the pattern can be obtained from the image sensor 12a. When the annular-looped illumination is used, the image signals including those of the opening 232 and the short-circuiting 234, differing from the pattern can be obtained from the image sensor 12a since the + first order diffraction light component in the X axis direction is not generated. When the annular-looped illumination is used, generation of, for example, the 0th order diffraction light from the discoloration defect 233 differs from that from an area where there is no discoloration defect, and the image signal showing the discoloration defect 233 can be obtained from the image sensor 12a.

FIG. 25 shows a case that the detection pixel to be sampled in the A/D converter 15a with respect to the LSI wafer pattern shown in FIG. 24 is large. In the case that the detection pixel 241 to be sampled in the A/D converter 15a is large as shown in FIG. 25, two edges of the pattern remain in one detection pixel 241 and the edge information of the pattern will be lost.

To prevent loss of the edge information of the pattern, the dimensions of the detection pixel 241 to be sampled in the A/D converter 15a can be reduced. When the dimensions of the detection pixel are reduced, sampled digital image signal information obtained from the A/D converter 15a increases, a volume of defect detection image signal information to be processed in the comparator circuit 17 also increases and therefore it takes a lot of time to detect the defect. Accordingly, as shown in FIG. 27, the pattern A—A' can be sampled in a detection pixel size that the minimum and maximum values of brightness of the pattern are preserved, and converted to the digital image signals showing the shade (brightness).

The CPU 20 calculates an interval between the minimum value (edge information of the pattern) and the maximum value of the brightness of the pattern from a digital image signal 41 (shown in FIG. 27(a)) obtained from the A/D converter 15a by reducing the pixel size to be sampled by the A/D converter 15a, and sets a detection pixel size by which these minimum and maximum values can be divided. The A/D converter 15a carries out sampling according to the detection pixel size 42 set in the CPU 20 and therefore the digital image signal (shown in FIG. 27(b)) showing the shade (brightness) which is sampled in a relatively large detection pixel size can be obtained without losing the edge information of the pattern. Consequently, the volume of information for processing the defect detection image to be carried out in the comparator circuit 17 and others can be reduced and the defect can be detected in high speed and reliability.

Referring to FIG. 27(a), the CPU 20 sets the pixel size to be sampled to be small for the A/D converter 15a, selects X1/2 as the detection pixel size among X1, X2, X3 and X4 portions which have the relation of X1=X2=X3=X4 from the digital image signal 41 obtained from the A/D converter 15a, and sets X5 and X6 portions where the interval between the minimum value and the maximum value is large so that the detection pixel size is $3X_1/2$ and $2X_1$. A signal 42 corresponding to the detection pixel size which is set as described above is supplied to the A/D converter 15a.

FIG. 27(b) shows a waveform of a digital image signal sampled in the A/D converter 15a according to the signal 42 supplied from the CPU 20 for the waveform of the image signal of A—A' part shown in FIG. 27(a). As known from FIG. 27(b), in the A/D converter 15a, the digital image signals which contain the minimum and maximum values showing the pattern edge are obtained from the image signals outputted from the image sensor 12a. With this, the image signals showing the pattern edge to be obtained in high resolution are erased and a defect can be inspected with high reliability at a high speed by cell-comparing or chip-comparing digital image signals which are delayed as far as the cell interval or the chip interval in the delay memory 16 and the digital image signals directly obtained from the A/D converter 15a. The image signals indicating the pattern edge are repeated at the cell interval or the chip interval and simultaneously detected in cell comparison or chip comparison in the comparator circuit 17 and the image signal indicating the pattern edge can be erased. Consequently, a signal 18 indicating a defect can be detected unmatched in cell or chip comparison in the comparator circuit 17.

The CPU 20 can set the detection pixel size to $X=X_1/4$ or $X_1/8$ to carry out sampling of digital image signals between the minimum value and the maximum value. Thus, the A/D converter 15a can obtain the digital image signals showing the shade (brightness) from sampling in the above set detection pixel size ($X=X_1/4$ or $X_1/8$). In this case, the sampling interval is reduced and therefore high resolution image signals obtained from the image sensor 12a can be faithfully converted to the digital image signals.

The CPU 20 can vary the magnification of the image received by the image sensor 12a according to the digital image signal 41, which is obtained from the A/D converter 15a by reducing the pixel size to be sampled for the A/D converter 15a, by controlling the zoom lens 13 with a zoom lens control signal 43 as shown in FIG. 1. Consequently, even though the signal 42 for determining the detection pixel size is fixed in the A/D converter 15a, the detection pixel size to be sampled can be varied in accordance with the magnification depending on the zoom lens 13. Accordingly, for varying the magnification depending on the zoom lens 13, the zoom lens can be controlled with a command from the CPU 20.

Figure 28A:
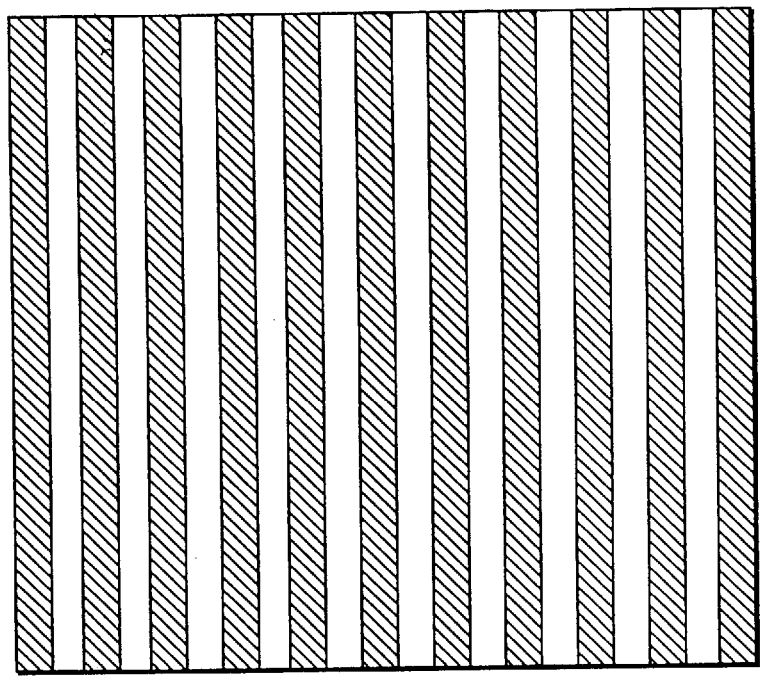
FIGS. 28(a) and 28(b) show an image signal waveform corresponding to a brightness which is faithfully obtained when the size of the pixel to be detected is set to 0.0175 μm for a grid repetitive pattern comprising lines of 0.42 μm in width and spaces.

In addition, sampling of high resolution image signals obtained by receiving the 0th order diffraction light 22a and the + first order diffraction light 25a, which are generated from the grid pattern by the annular-looped illumination and entered into the pupil 10a of the objective lens 9, in the A/D converter 15a is described with reference to FIGS. 28, 29 and 30. The grid pattern (wafer pattern formed with lines and spaces) respectively shown in FIGS. 28(a) to 30(a) is a repetitive pattern comprising lines of 0.42 μm in width and spaces of 0.42 μm in width which are repeated at the pitch P of 0.84 μm.

Figure 28B:
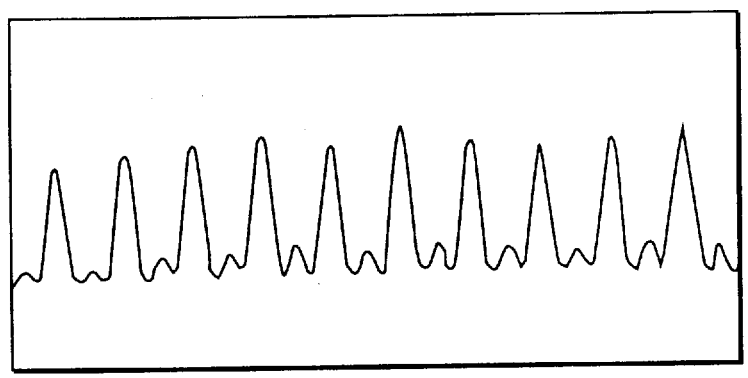

The waveform of the sampled digital image signal showing the shade (brightness) shown in FIG. 28 (b) is obtained when the detection pixel size is set to 0.0175 μm and it is known that the edge information of the grid pattern is clearly detected. In other words, it is indicated that high resolution image signals obtained by being received by the image sensor 12a are faithfully converted to the digital image signal indicating the shade (brightness) by the A/D converter 15a.

Figure 29A:
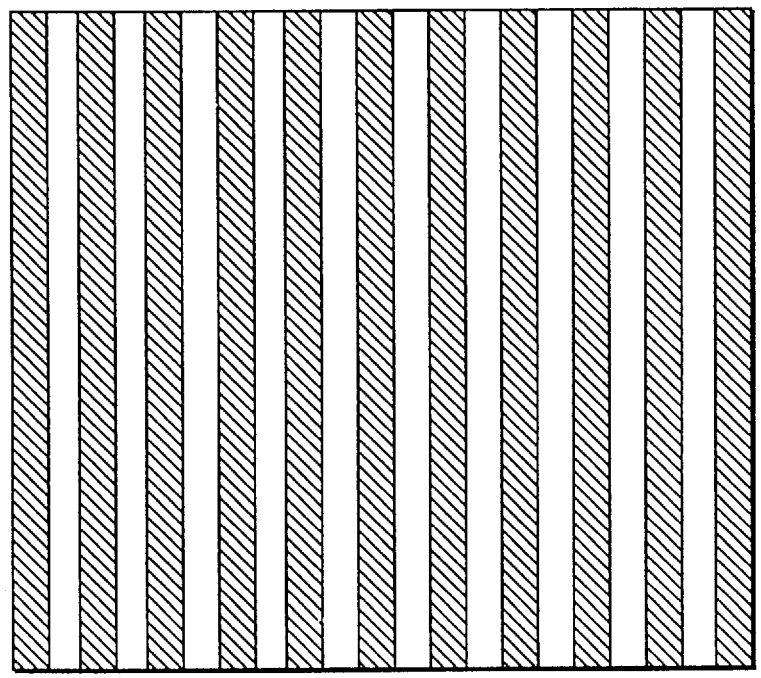
FIGS. 29(a) and 29(b) show an image signal waveform corresponding to a brightness for which a maximal value is maintained when the size of the pixel to be detected is set to 0.14 μm for a grid repetitive pattern comprising lines of 0.42 μm in width and spaces.
Figure 29B:
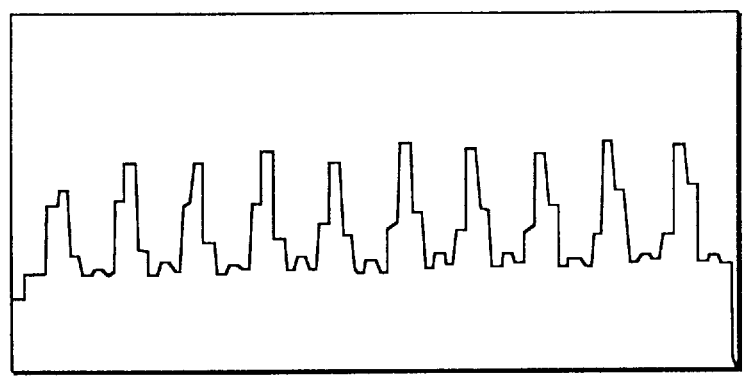
Figure 30A:
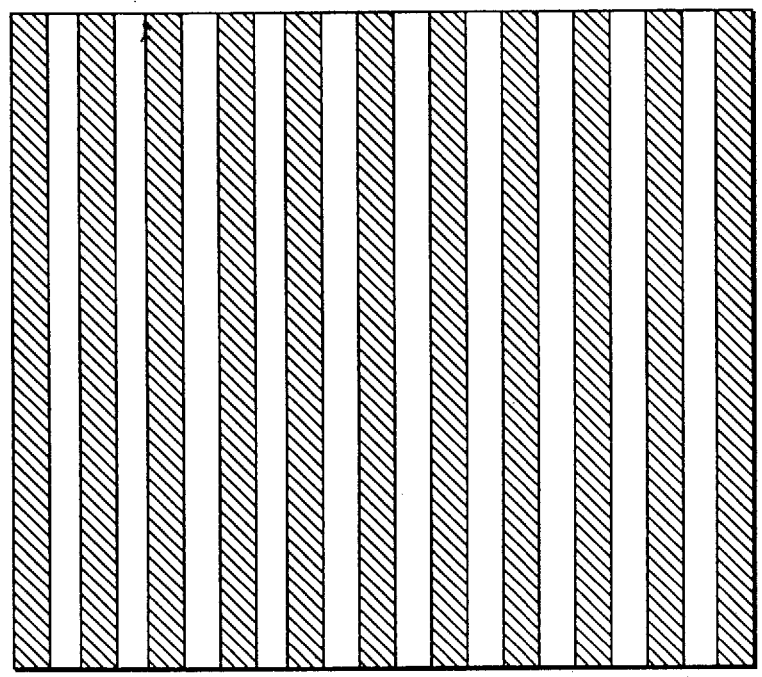
FIGS. 30(a) and 30(b) show an image signal waveform corresponding to a brightness for which a maximal value is not maintained when the size of the pixel to be detected is set to 0.28 μm for a grid repetitive pattern comprising lines of 0.42 μm in width and spaces.

The waveform of the sampled digital image signal showing the shade (brightness) shown in FIG. 29 (b) is obtained when the detection pixel size is set to 0.14 μm and it is known that the edge information (information of ultimate values such as minimum and maximum values) of the grid pattern is detected as being stored.

Figure 30B:
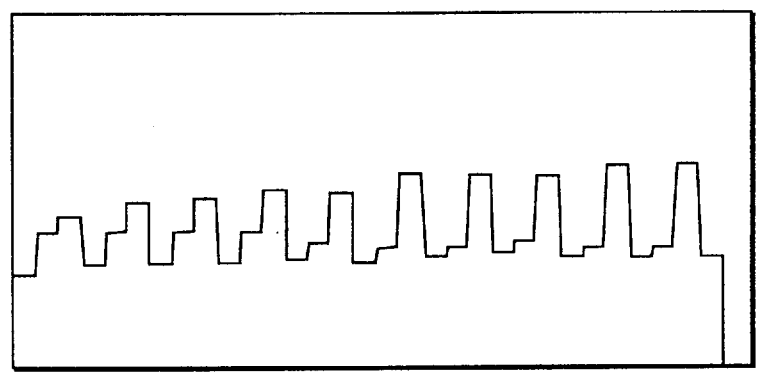

The waveform of the sampled digital image signal showing the shade (brightness) shown in FIG. 30 (b) is obtained when the detection pixel size is set to 0.28 μm and it is known that the edge information (information of ultimate values such as minimum and maximum values) of the grid pattern is detected as being partly missed.

Therefore, the repetitive pattern (grid pattern) comprising lines of 0.42 μm in width and spaces of 0.42 μm in width which are repeated at the pitch P of 0.84 μm should be converted to the digital image signal indicating the shade (brightness) by sampling in the A/D converter 15a while setting the detection pixel size to be set according to the signal 42 from the CPU 20 to approximately 0.3 μm or less. With this, the edge information (information of ultimate values such as minimum and maximum values) of the grid pattern is detected as being stored in the digital image signal showing the shade (brightness) and can be detected as being discriminated from the defect and therefore those defects (projection 231, opening 232, discoloration 233, short circuiting 234, chipping 235 and stain 236, etc.) can be detected through cell comparison or chip comparison in the comparator circuit 17.

When sampling in which the minimum and maximum values of the pattern are preserved is executed in the A/D converter 15a, the pattern information is not damaged even in case of a large detection pixel size and high precision defect inspection can be carried out at a high speed in the comparator circuit 17.

In the embodiments shown in FIGS. 28 to 30, the waveform of the sampled digital image signal indicating the shade (brightness) is described with a one-dimensional grid pattern and it is apparent that these embodiments can also apply to a two-dimensional grid pattern.

The above-described embodiments include the embodiment for inspecting a defect on the pattern formed on the inspected object 1 and the embodiment of the microscopic observation system for observing the pattern formed on the inspected object 1. The present invention can apply as a fifth embodiment to inspection of impurities which remain on the pattern formed on the inspected object 1 and measurement of the dimensions of the pattern formed on the inspected object 1.

As described in the fourth embodiment, for example, the CPU 20 can measure the dimensions of the pattern with high accuracy. Impurities which exist on the pattern (LSI wafer pattern) formed on the inspected object 1 can be detected as in inspection of defects. In other words, the first order or higher order diffraction lights which have various diffraction angles are introduced from impurities into the pupil 10a of the objective lens 9 as in the case of projection defect 231 and chipping defect 236. On the other hand, the 0th order diffraction light and the + first order diffraction light from the pattern are entered into the pupil 10a of the objective lens 9, different image signals are detected from the image sensor 12a, and impurities can be detected by cell comparison or chip comparison executed in the comparator circuit 17. Those impurities on a mirror surface wafer can be similarly detected.

As described in the following embodiments, the information of the pattern can be erased by using a space filter 309 not erased by cell comparison or chip comparison. Impurities can be detected according to the image signals on the pupil 10a of the objective lens 9 which are detected by the image sensor 12b. In other words, the impurities on the mirror surface wafer can be directly detected from the image signals on the pupil 10a of the objective lens 9 detected by the image sensor 12b. Impurities which exist on the pattern (LSI wafer pattern) formed on the inspected object 1 can be detected by erasing the pattern information from the image signals on the pupil 10a of the objective lens 9 detected by the image sensor 12b, since the locality distribution of the diffraction lights entering into the pupil 10a of the objective lens 9 is different between the impurities and the pattern.

Specifically, the impurities can be detected by storing the reference image signals on the pupil 10a obtained from a normal pattern on which no impurities exist and which is detected by the image sensor 12b in the delay memory 16, and comparing the stored reference image signals on the pupil 10a and the image signals on the pupil 10a obtained from the inspected pattern to be actually detected by the image sensor 12b to erase the pattern information. The pattern information can be erased and the impurities can be detected by masking (shielding) the locality distribution information of the diffraction lights on the pupil 10a to be obtained from the inspected pattern with the locality distribution information or the reversed locality distribution information (space filter 309 in FIGS. 31 and 33) of the diffraction lights on the pupil 10a to be obtained from the normal pattern.

Figures 31, 32:
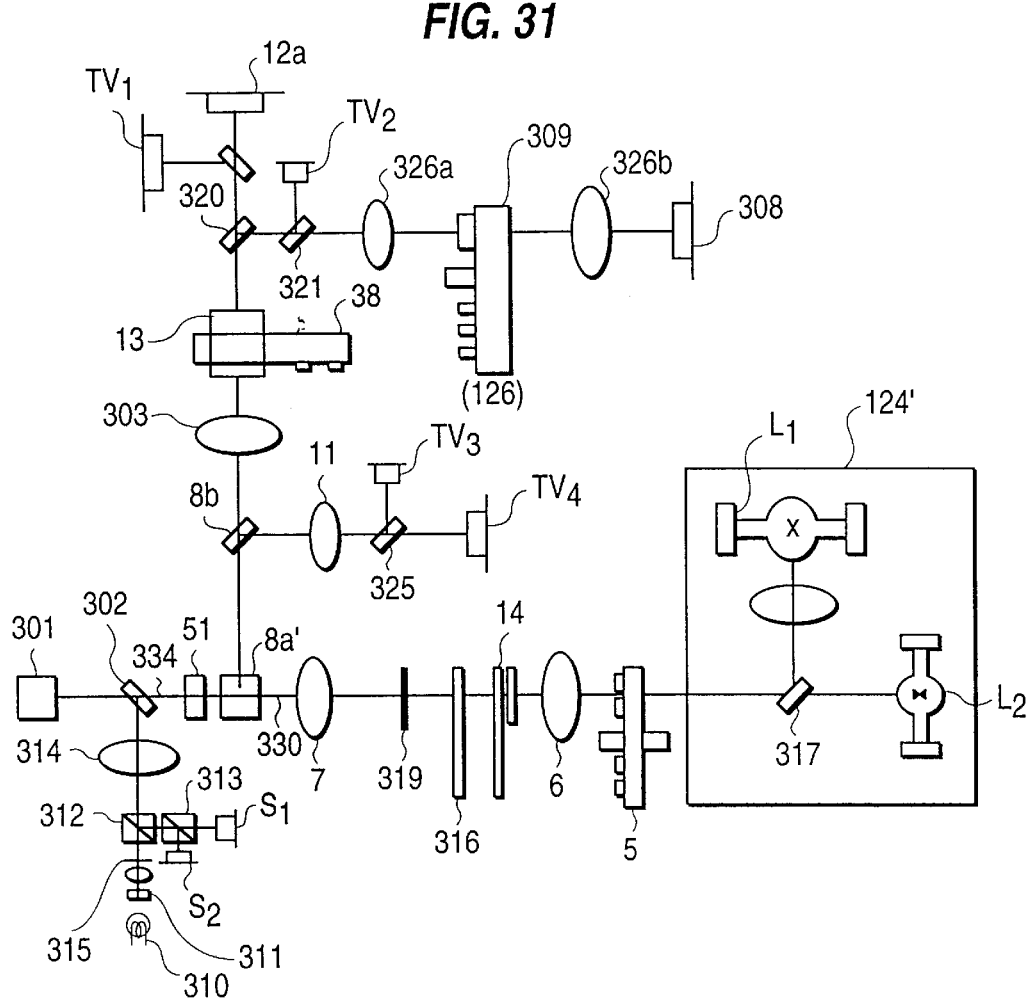
FIG. 31 illustrates an optical system in an embodiment of the pattern inspection apparatus shown in FIG. 1 according to the present invention for inspecting a defect of the pattern on the object to be inspected.
FIG. 32 is a front view of FIG. 31.

A practical configuration of an optical system for use in the pattern inspection apparatus according to the present invention as a sixth embodiment is described with reference to FIGS. 31 and 32, which respectively show the practical configuration of the optical system to be used in the pattern inspection apparatus shown in FIG. 1, wherein FIG. 31 is a plan view and FIG. 32 is a front view thereof.

The configuration of the optical system shown in FIGS. 31 and 32 for use in the pattern inspection apparatus is basically the same as the configuration of the optical system shown in FIG. 1 for the pattern inspection apparatus. In this embodiment, a television camera $TV_1$ for annular-looped illumination (bright field illumination) and a television camera $TV_2$ for dark field illumination as TV cameras for observing images, and a television camera $TV_4$ for dark field illumination as a TV camera for observing the pupil 10a of the objective lens 9 are added. Accordingly, the TV camera $TV_1$ for annular-looped illumination (bright field illumination) and the TV camera $TV_2$ for dark field illumination are used to observe the images. The TV camera $TV_3$ for annular-looped illumination (bright field illumination) to be used as the TV camera for observing the pupil 10a of the objective lens 9 is the same as the image sensor 12b.

Specifically, based on an image (a locality distribution of the diffraction light obtained from the pattern on the inspected object 1 with annular-looped illumination) on the pupil 10a to be picked up by the TV camera $TV_3$ (12b) for annular-looped illumination (bright field illumination), the CPU 20 selectively controls a defect detection sensitivity in the filter (disc type mask: opening diaphragm) 5 for annular-looped illumination, the pupil filter (attenuation filter) 38 for controlling the light quantity of the 0th diffraction light or the comparator circuit 17; a detection pixel size to be obtained from sampling by the A/D converter 15a; or a magnification depending on the zoom lens 13. Based on the image (a distribution of scattering light to be obtained from the pattern on the inspected object 1 with dark field illumination described later) on the pupil 10a to be picked up by the TV camera $TV_4$ for dark field illumination, the CPU 20 selectively controls an impurity detection sensitivity in the space filter 309 or the comparator circuit, or the detection pixel size to be obtained from sampling by the A/D converter for A/D-converting the image signals obtained from a linear image sensor 308. Thus, the microscopic observation system can be adapted for the pattern on the inspected object 1.

A dichroic mirror 325 admits to pass a light of the image on the pupil 10a as the diffraction light to be obtained from the inspected object 1 with the annular-looped illumination of 600 nm or under in wavelength, and reflects a light of the image on the pupil 10a as the scattering light to be obtained from the inspected object 1 with the dark field illumination of 780 to 800 nm in wavelength, which is described later. Reference numerals 326 is a mirror.

The light house 124' comprises two types of lamps, that is, a Hg-Xe lamp $L_1$ and a Xe lamp $L_2$ as the primary light sources 3 and 4 shown in FIG. 1 and these two types of the primary light sources are adapted to be changed over by a mirror 317 for changeover. The Hg-Xe lamp $L_1$ has a brightness spectrum and is available for high intensity illumination with a width of short wavelength and the Xe lamp $L_2$ can provide incandescent illumination. In other words, for annular-looped illumination including circular illumination through the filter 5 for annular-looped illumination (secondary light source for annular-looped illumination: disc type mask: opening diaphragm), the illumination can be made by changing over high intensity illumination at the width of short wavelength using the Hg-Xe lamp $L_1$ and incandescent illumination using the Xe lamp $L_2$.

Figure 33:
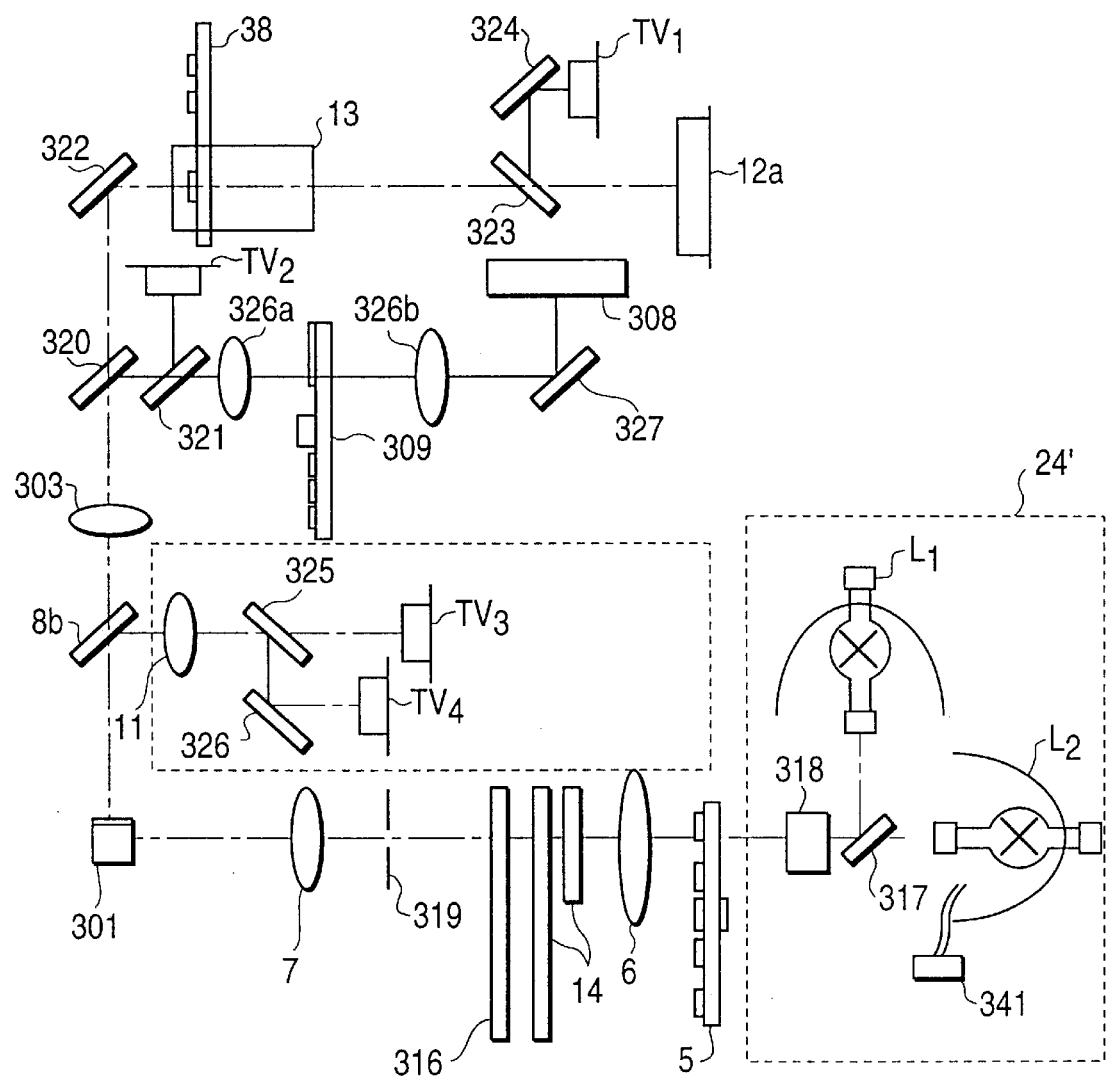
FIG. 33 is a plan view further specifically showing the embodiment shown in FIG. 31.

An integrator 318 as shown in FIG. 33, is provided for making uniform the intensity of light emitted from the Hg-Xe lamp $L_1$ or the Xe lamp $L_2$ and an intensity monitor 341 is provided for monitoring variations of the intensity of light in the primary light sources $L_1$ and $L_2$. The light quantity control filter 14 is controlled and the conversion level in the A/D converter 15 is compensated, in accordance with the variations of the intensity in the primary light sources $L_1$ and $L_2$ monitored by an intensity monitor 341, as shown in FIG. 33. A wavelength selection filter 316 is provided for selecting the wavelength of the annular-looped illumination light to, for example, 600 nm or under. A field diaphragm 319 is provided for shielding a light other than the annular-looped illumination and a mirror 301 is also provided.

A dichroic mirror 320 provided in the front of a second objective lens 303 is intended to pass the diffraction light obtained from the inspected object 1 with the annular-looped illumination of wavelength of 600 nm or under, and reflect a scattering light obtained from the inspected object 1 with the dark field illumination of wavelength of 780 to 800 nm described later. There is also provided a half mirror 321 and lenses 326a and 326b. A space image formed with a scattering light produced from the pattern on the inspected object 1 with the dark field illumination of wavelength of 780 to 800 nm is formed at the position of the space filter 309. Further, there is provided mirrors 322, 324 and 327 and a half mirror 323, as shown in FIG. 33.

In addition, a dark field illumination optical system (304, 305, 306 and 307) for focusing a laser beam emitted from a semiconductor laser beam source $L_3$ and slantly irradiating the laser beam onto the inspected object 1 (LSI wafer) is provided so that the impurities can be detected with high sensitivity. A beam expander 304 (beam expanding optical system) is provided for the diameter of the laser beam emitted from the semiconductor laser beam source $L_3$ and mirrors 305 and 306 are provided for reflecting the laser beam while a focusing lens 307 is provided for focusing the laser beam the diameter of which is expanded and slantly irradiating the laser beam onto the inspected object 1.

The 0th order diffraction light (positive reflection light) produced from the inspected object 1 with dark field illumination by the dark field illumination optical system (304, 305, 306 and 307) is not entered into the pupil 10a of the objective lens 9 and only the scattering light (first order or higher order diffraction light) produced from impurities on the inspected object 1 is entered into the pupil 10a of the objective lens 9 and received by the image sensor 308, which outputs the signals to enable detection of the impurities. A space filter 309 is provided which shuts off to erase the scattering light (first order or higher order diffraction light) which is produced from the pattern edge on the inspected object 1 with the dark field illumination and entered into the pupil 10a of the objective lens 9. The wavelength of the laser beam emitted from the semiconductor laser beam source $L_3$ is an optional wavelength, for example, 780 to 800 nm, different from the wavelength of the annular-looped illumination (bright field illumination) from the light house 124'.

In addition, an automatic focus control optical system is provided to detect the pattern on the inspected object 1 with high accuracy as the image signals by the image sensor 12a. This automatic focus control optical system comprises a light source 310, a filter 313 for obtaining a wavelength of 600 to 700 nm, a pattern 315 for automatic focus (A/F), a projector lens 314 for projecting the pattern 315 for A/F on the inspected object 1, half mirrors 312 and 313, and sensors $S_1$ and $S_2$ arranged in the front and back of focusing plane.

The surface (pattern surface) of the inspected object 1 is focused with the objective lens (imaging optical system) 9 by slightly controlling the inspected object 1 in the vertical direction as shown with an arrow mark so that the contrast signals of the A/F pattern 315, which is projected onto the inspected object 1 by the projector lens 314, are respectively detected by the sensors $S_1$ and $S_2$, and the contrast signal obtained from the sensor $S_1$ coincides with the contrast signal obtained from the sensor $S_2$. The dichroic mirror 302 provided in the light path of the detection optical system reflects a light of 600 to 700 nm in wavelength for automatic focusing and admits to pass a light of 600 nm or under in wavelength for annular-looped illumination (bright field illumination) and a light of 750 nm or over in wavelength for dark field illumination.

Figure 34:
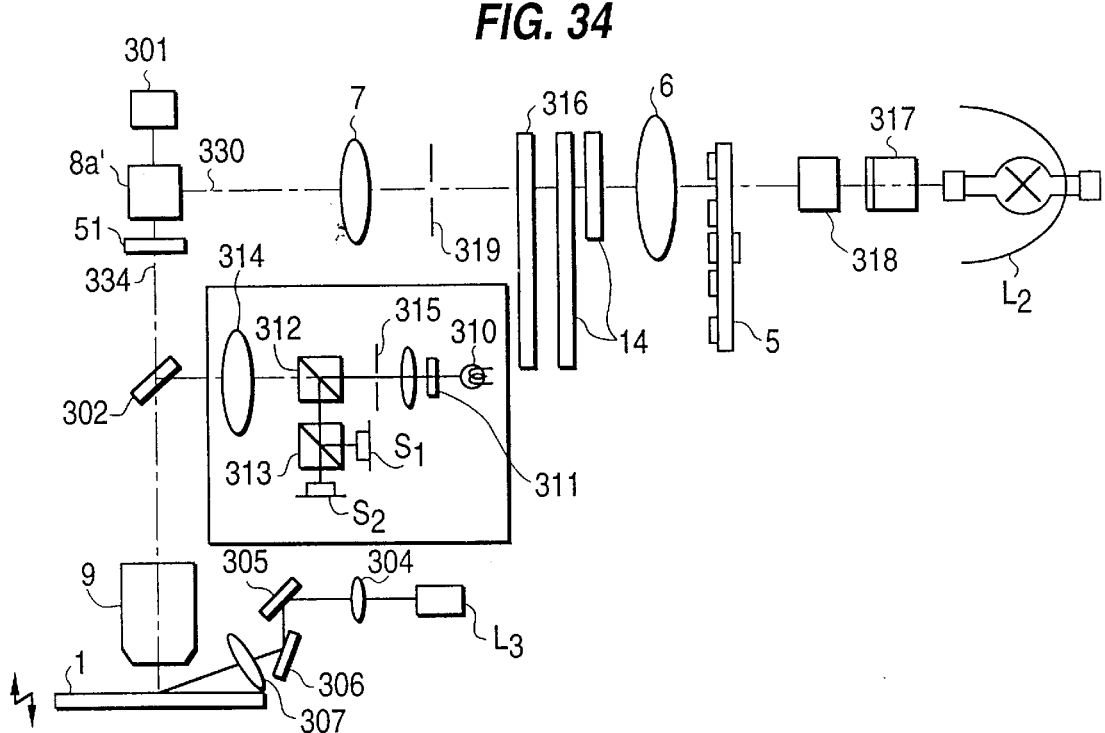
FIG. 34 is a front view of FIG. 33.

FIGS. 33 and 34 respectively show further in detail the configuration of the optical system in the pattern inspection apparatus shown in FIGS. 31 and 32. FIG. 33 is a plan view and FIG. 34 is a front view. In other words, an infinite compensation type objective lens 9 is used and therefore a second objective lens (also referred to as tube lens) 303 with a long focal distance (for example, f=200 nm) is required. The linear image sensor 12a for annular-looped illumination (bright field illumination) and the linear image sensor 308 for dark field illumination are formed with a TDI (Time Delay & Integration) type image sensor.

Figure 35:
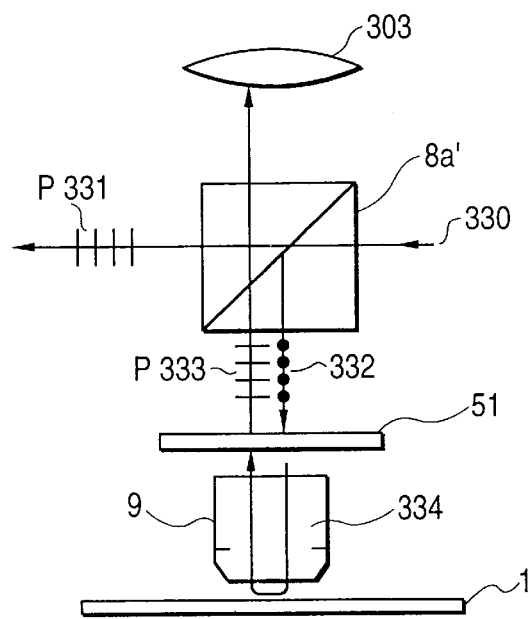
FIG. 35 is a diagram showing an embodiment of an optical system for circular polarization illumination.
Figure 36:
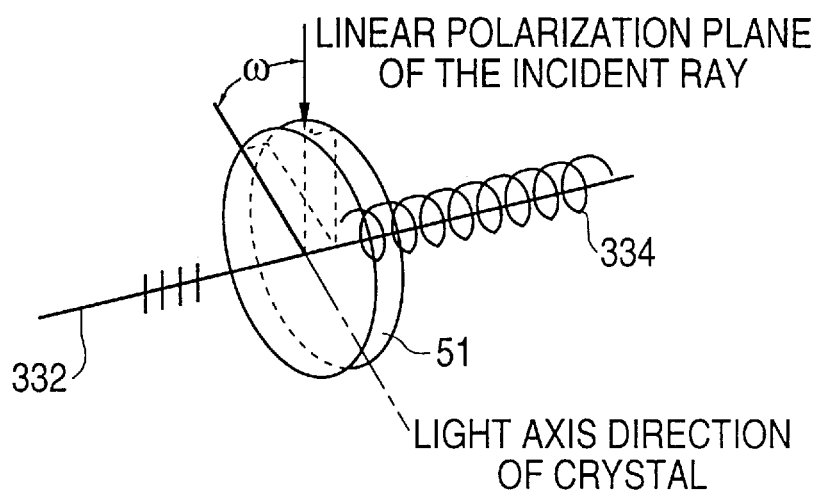
FIG. 36 is a diagram for describing conversion from linear polarization to circular or elliptic polarization with a ¼ wavelength plate.

In this embodiment, a polarization beam splitter (PBS) 8a' and a λ/4 plate (¼ wavelength plate) 51 are provided between the objective lens 9 and a second objective lens 303. Since the lights remain parallel between the objective lens 9 and the second objective lens 303, any deterioration such as aberration is not caused even though the above optical elements 8a' and 51 are inserted. The functions of the PBS 8a' and the λ/4 plate 51 are as shown in FIGS. 35 and 36. Of circular illumination light or annular-looped illumination light 330, P polarization light passes through the PBS 8a' and S polarization light is reflected to reach the λ/4 plate 51. The S polarization light 332, which has reached the λ/4 plate 51 to include a component the phase of which is delayed equivalent to 90 degrees (the refractive indexes of an extraordinary ray and an ordinary ray are unequal and the length of the optical path of the extraordinary ray is longer than the latter. Therefore, a phase difference π/2 occurs between the extraordinary ray and the ordinary ray and the amplitudes of these rays are equal.), is converted to circular polarization light or elliptical polarization light 334 and irradiated onto a wafer which is the inspected object 1 through the objective lens 9.

The diffraction light (reflection light) entering into the pupil 10a of the objective lens 9 reaches again the λ/4 plate 51 and the circular polarization light or the elliptical polarization light becomes the P polarization light 333. This P polarization light 333 transmits through the PBS 8a' and the second objective lens 303 and reaches the image sensor 12a as the detector. FIG. 36 indicates that, when the angle ω to the λ/4 wavelength plate 51 (angle formed by the linear polarization plane of the incident light and the main cross section of the wavelength plate 51) of the incident light (S polarization light) 332, which is converted to the linear polarization light by the PBS 8a', is accurately 45° (+ or −), the incident light 332 of linear polarization can be converted to the circular polarization light 334 (or vice versa). When the angle ω is other than 450, the linear polarization light is converted to the elliptical polarization light 334 (or vice versa).

Figure 37:
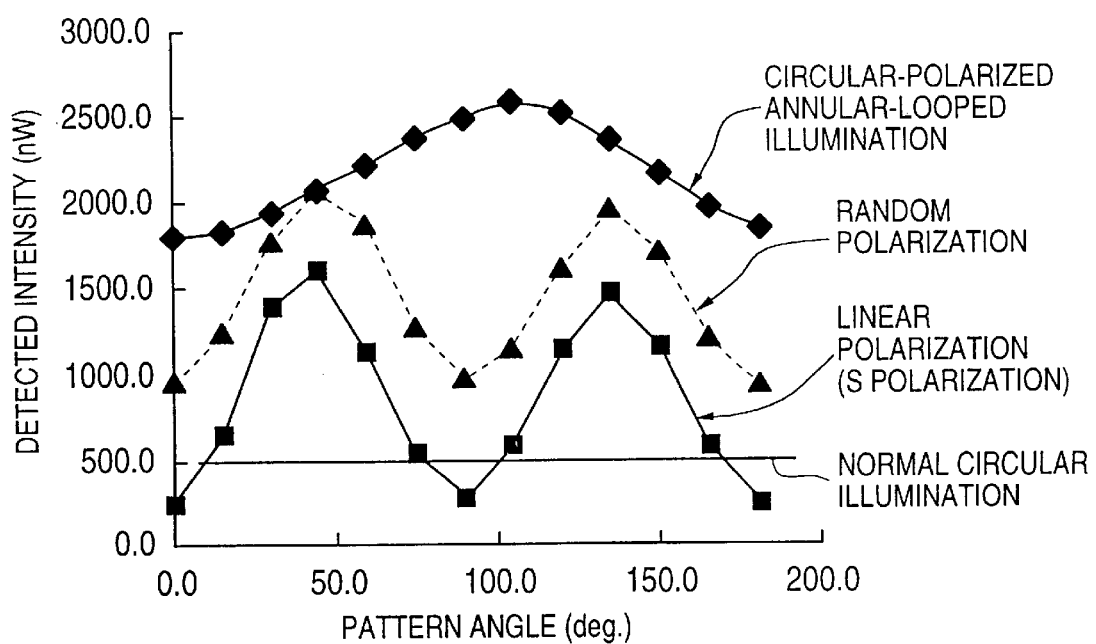
FIG. 37 shows a detection intensity corresponding to the brightness for a pattern angle in an experimental example for which a state of polarization in the annular-looped illumination is controlled.

FIGS. 37 and 38 show the effects of this embodiment. The inspected object 1 is a pattern comprising lines and spaces of a 256 Mb DRAM (a high density grid pattern with pitch P of 0.61 μm). FIG. 37 shows the brightness (detection intensity) of the pattern received by the image sensor 12a to the rotating direction of the above pattern. The circular polarization annular-looped illumination (including elliptic polarization annular-looped illumination) in FIG. 37 are based on the embodiments shown in FIGS. 31 to 34. The linear polarization illumination in the diagram corresponds to the illumination having no λ/4 plate 51. The half mirror in the diagram indicates an illumination (illumination using the λ/4 plate 51) for which a typical half mirror is used instead of the PBS 8a'.

From the relationship shown in FIG. 37, it is apparent that the image signals having high brightness (detection intensity) can be obtained from the image sensor 12a without being largely affected by the directionality of the pattern, by applying the circular polarization annular-looped illumination (including the elliptical polarization annular-looped illumination) even though a high density pattern on the inspected object 1 has various rotation angles as a memory cell pattern as shown in FIG. 24. By using the annular-looped illumination, whether linear polarization illumination (S polarization illumination) or half mirror illumination (using the λ/4 plate 51), the image signals having higher brightness (detection intensity) can be obtained from the pattern formed on the inspected object 1 which has a peripheral circuit part having a special directionality as compared with application of the only ordinary circular illumination.

It is apparent that the half mirror illumination (using the λ/4 plate 51) is superior to the linear polarization illumination (S polarization illumination). That the image signals having a high brightness (detection intensity) can be obtained from the image sensor 12a as described above means that highly efficient illumination for the high density pattern can be implemented.

FIG. 38 shows a contrast (a ratio of the minimum value to the maximum value indicating the resolution) from the pattern received by the image sensor 12a in the rotating direction of the pattern. In FIG. 38, the circular polarization annular-looped illumination (including elliptical polarization annular-looped illumination) is based on the embodiments shown in FIGS. 31 to 34. In the diagram, there is only circular polarization illumination, and linear polarization illumination corresponds to S polarization illumination without the λ/4 plate 51.

In case of circular polarization annular-looped illumination, the contrast to the angle of the pattern is not fixed because complete circular polarization is not obtained in the experiment and elliptical polarization appears. The ellipticity can be reduced to obtain a true circle by entering a linear polarization incident light into an optical element (λ/4 plate 51) (the direction of electric vector oscillation is aligned in parallel with or normal to the incident plane) and circular polarization is used by using the phase plate before entry into the inspected object 1.

From the relationship shown in FIG. 38, it is apparent that the image signals having a high contrast (high resolution) can be obtained from the image sensor 12a without being largely affected by the directionality of the pattern, by applying the circular polarization annular-looped illumination (including the elliptical polarization annular-looped illumination) even though a high density pattern on the inspected object 1 has various rotation angles as a memory cell pattern as shown in FIG. 24.

Those image signals having a high contrast can always be obtained from the image sensor 12a without depending on the direction of the high density pattern, by simultaneously using circular polarization illumination and annular-looped illumination and consequently micro fine defects on the high density pattern can be detected. The image signals having a high contrast (high resolution) can be obtained from simple combination of normal circular illumination and circular polarization illumination (only circular polarization illumination) without being largely affected by the directionality of the high density pattern from the image sensor 12a as compared with the normal circular illumination. The image signals having a higher contrast (high resolution) than in case of only circular polarization illumination can be obtained by simultaneously using the circular polarization illumination and the annular-looped illumination.

By using the annular-looped illumination, the image signals having the high contrast (high resolution) can be obtained from a high density pattern which is formed on the inspected object 1 and has a special directionality as the peripheral circuit part even with the linear polarization illumination (S polarization illumination). However, In cases of general super LSIs (VLSI and ULSI) on which high density patterns are provided and therefore it is difficult to irradiate the linear polarization light to these patterns at all times in accordance with the directions of high density patterns. If the patterns have a specified directionality as a specified wiring pattern, it is necessary to control the polarization in the linear polarization illumination to be aligned with the direction of the wiring pattern and to limit the linear polarization illumination only to the specified wiring pattern. In doing so, the image signals having the high contrast can be detected from the image sensor 12a.

Though the PBS 8a' is used in the description of the above embodiments, similar effects can be obtained by using the half mirror which is coated with a dielectric multi-layer film. A polarization plate can be used to obtain the linear polarization illumination instead of the PBS 8a'. In this case, the quantity of light passing through the polarization plate is attenuated and the brightness (detection intensity) is decreased but the contrast is improved as in case of the PBS 8a'.

In a seventh embodiment of the present invention, a diffusion plate for diffusing light is inserted into the position (position in conjunction with the pupil 10a of the objective lens 9) of the field diaphragm 319 or the filter (opening diaphragm) 5 for annular-looped illumination. This diffusion plate is specified with the sand No. 800. Such diffusion plate serves to increase a diffusibility of the illumination light in irradiation of only the annular-looped illumination light or simultaneous irradiation of the polarized illumination and the annular-looped illumination to the inspected object 1, and a bright and uniform reflection light can be obtained in spite of the variation of the surface of metallic wiring pattern, such as fine recesses and projections and therefore the surface of the metallic wiring pattern can be detected or observed as the image having uniform brightness by the image sensor 12a or the TV camera $TV_1$ for bright field observation through the objective lens 9.

This diffusion illumination is not compatible with annular-looped illumination and polarization illumination and can be simultaneously implemented in the same optical system. The extent of diffusion is selected in accordance with the pattern on the inspected object 1.

In the embodiments shown in FIGS. 31 to 34, the image sensor 12a is formed with the TDI (Time Delay & Integration) type image sensor and, if the reflectivity of the pattern of the inspected object 1 is low and the brightness (detection intensity) is insufficient, the image sensor can be controlled to increase its accumulation time. Thus, the accumulation time of the image sensor can be appropriately determined in accordance with the pattern of the inspected object 1. Furthermore, the accumulation time of the image sensor can be determined according to the illuminating conditions for the pattern of the inspected object 1.

The following describes analyses of the causes of defects, for example in semiconductor manufacturing processes as shown in an eighth embodiment of the present invention as illustrated in FIG. 39, by entering defect determination output 18 to be outputted from the comparator circuit 17 of the apparatus shown in FIG. 1 and defect information 40 to be outputted from the CPU 20, and production of high quality semiconductor chips at a high yield by eliminating the analyzed causes of defects.

As shown in FIG. 39, there is provided a semiconductor manufacturing line 380 with a conveying path 381 for a semiconductor wafer 1a. A CVD unit 382 is provided for executing a CVD film forming step for forming an insulation film and a sputtering unit 383 is provided for executing a sputtering step for forming a wiring film of the semiconductor steps. An exposure unit 384 is provided for executing exposure steps for application of resist, exposure and development of the semiconductor manufacturing steps and an etching unit 385 is provided for executing an etching step for patterning of the semiconductor manufacturing steps. Thus, semiconductor wafers are manufactured through various manufacturing steps.

A computer 390 is provided for analyzing the causes of defects or factors of defects in the manufacturing line 380 comprising the process units 382, 383, 384 and 385 for manufacturing the above-described semiconductors by entering defect determination output 18 outputted from the comparator circuit 17 and defect information 40 outputted from the CPU 20 shown in FIG. 1. The computer 390 for analysis comprises an interface 391 for entering the defect determination output 18 outputted from a comparator circuit 17 and the defect information 40 outputted from the CPU 20 shown in FIG. 1; a CPU 392 for executing processing such as analysis; a memory 393 which stores programs such as for analysis; control circuits 394, 395, 396 and 397; an output unit 398 such as a printing unit for outputting the results of analysis such as causes of defects; a display unit 399 for displaying various data; an input unit (comprising a keyboard, a disc and others) 401 for entering data related to, for example, process units 382, 383, 384 and 385 which cannot be obtained from the units shown in FIG. 1 and data related to the semiconductor wafer 1a to be supplied to the manufacturing line 380; an external storage unit 402 which stores history data of correlation between defects which occur on the semiconductor wafer 1a and the causes of defects or the factors of defects due to which a defect is caused in the manufacturing line 380 which comprises process units 382, 383, 384 and 385, or a data base; an interface 403 for supplying information 410 related to the causes of defects or the factors of defects analyzed by the CPU 392 to the process units 382, 383, 384 and 385; and a bus line 400 for connecting these component units.

The CPU 392 in the computer 390 for analysis analyzes the causes of defects or the factors of defects due to which a defect is caused in the manufacturing line 380 which comprises process units 382, 383, 384 and 385 according to the defect determination output 18 and the defect information 40, and the history data of correlation between defects on the semiconductor wafer 1a and the causes of defects or the factors of defects in the manufacturing line 380 or a data base, which are stored in the external storage unit 402, and supplies the information 410 related to the analyzed cause or factor of defect to the process units 382, 383, 384 and 385.

The process units 382, 383, 384 and 385 to which the information 410 related to the causes of defects or the factors of defects is supplied can feed a satisfactory semiconductor wafer 1a to a following process by controlling various process conditions including cleaning, and by eliminating the causes of defects or the factors of defects and consequently manufacture semiconductors at a high yield. The semiconductor wafer 1a, a defect of which is inspected by the apparatus shown in FIG. 1, is sampled in a unit of the semiconductor wafer 1a or a lot thereof in the front and rear processes where the defect is liable to be caused in the manufacturing line 380.

The CPU 392 in the computer 390 for analysis analyzes the causes of impurities or the factors of impurities due to which an impurity is caused in the manufacturing line 380 according to impurity information obtained from and entered by the CPU 20 in accordance with an impurity signal detected by an image sensor 308, and the history data of correlation between the impurities on the semiconductor wafer 1a and the causes of impurities or the factors of impurities due to which an impurity is formed in the manufacturing line 380 or a data base, which are stored in the external storage unit 402, and supplies the information 410 related to the analyzed cause or factor of impurity to the process units 382, 383, 384 and 385.

The process units 382, 383, 384 and 385 to which the information 410 related to the causes of impurities or the factors of impurities is supplied can feed a defect-free semiconductor wafer 1a to a following process by controlling various process conditions including cleaning, and by eliminating the causes of impurities or the factors of impurities and consequently manufacture semiconductors at a high yield.

The present invention enables inspection with high reliability of micro fine defects which occur on micro fine patterns formed on a semiconductor substrate having micro fine patterns such as a semiconductor wafer, a TFT substrate, a thin film multi-layer substrate and a printed board, and to manufacture semiconductor substrates at a high yield by feeding back the results of inspection to the manufacturing processes for semiconductor substrates. In addition, the present invention is adapted to detect defects on micro fine patterns by detecting high resolution image signals from micro fine patterns on the inspected object with annular-looped illumination applied thereto, comparing these high resolution image signals with the reference high resolution image signals and erasing micro fine patterns according to consistency of these image signals to detect the defects on the micro fine patterns and therefore, provides an effect to inspect the defects on micro fine patterns in high reliability.

The present invention is adapted to irradiate the annular-looped illumination onto micro fine patterns on the inspected object, attenuate at least part of the 0th order diffraction light of the 0th order diffraction light and the first order diffraction light (+ first order diffraction light or − first order diffraction light), which are produced from the micro fine pattern and entered into the pupil of the objective lens, by the filter for controlling the light quantity which is provided at a position in conjunction with the pupil of the objective lens, receive the 0th order diffraction light and the first order diffraction light, detect image signals of high resolution from the micro fine pattern, compare the high resolution image signals with the reference high resolution image signals, erase the micro fine pattern according to consistency of these image signals, and detect the defects on the micro fine pattern, and therefore provides an effect to inspect the defects on micro fine patterns in high reliability. Further, the present invention enables detection of the images or image signals from the micro fine patterns in a high resolution (resolution power) and a large difference of shade (brightness), by simultaneously using the annular-looped illumination and the polarization illumination (particularly, circular or elliptic polarization illumination is excellent) for micro fine patterns on the inspected object. The present invention provides an effect enabling to detect the images or image signals from the micro fine patterns having various directionalities in a high resolution (resolution power) and a large difference of shade (brightness), by simultaneously using the annular-looped illumination and the polarization illumination (particularly, circular or elliptic polarization illumination is excellent) for micro fine patterns having various directionalities on the inspected object.

The present invention is adapted to detect the image signals having a high resolution (resolution power) and a large difference of shade (brightness) from the micro fine patterns having various directionalities on the inspected object by simultaneously using the annular-looped illumination and the polarization illumination (particularly, circular or elliptic polarization illumination is excellent) for micro fine patterns, compare these image signals with the reference image signals having a high resolution (resolution power) and a large difference of shade (brightness), erase the micro fine patterns having various directionalities according to consistency of these image signals, to detect the defects on the micro fine patterns having various directionalities, and therefore provides an effect of inspecting the defects of micro fine patterns having various directionalities in high reliability.

The present invention enables detection of images or image signals with a high resolution (resolution power) adapted to a micro fine pattern by detecting an image based on a diffraction light which is produced from a micro fine pattern on the inspected object and entered into the pupil of the objective lens, controlling the annular-looped illumination (for example, OUT σ and IN σ) according to this image, and applying this controlled annular-looped illumination to the micro fine pattern on the inspected object. Further, the present invention is adapted to detect the defects on the micro fine pattern by detecting an image based on a diffraction light which is produced from a micro fine pattern on the inspected object and entered into the pupil of the objective lens, controlling the annular-looped illumination (for example, OUT σ and IN σ) according to this image, applying this controlled annular-looped illumination to the micro fine pattern on the inspected object to detect the image signals of a high resolution (resolution power) adapted to a micro fine pattern, comparing these image signals having a high resolution with the reference image signals having a high resolution, and erasing the micro fine pattern according to consistency of these image signals to detect the defects on the micro fine pattern and therefore provides an effect enabling to inspect the defects on the micro fine pattern in high reliability.

Additionally, the present invention enables detection of images or image signals with a high resolution (resolution power) adapted to a micro fine pattern by identifying (observing or detecting) a locality distribution of the 0th order diffraction light and the first order diffraction light (+ first order or − first order diffraction light) which are produced from a micro fine pattern on the inspected object and entered into the pupil of the objective lens, controlling the annular-looped illumination (for example, OUT σ and IN σ) according to this identified (observed or detected) locality distribution of the diffraction light, and applying this controlled annular-looped illumination to the micro fine pattern on the inspected object.

The present invention is adapted to identify (observe or detect) a locality distribution of the 0th order diffraction light and the first order diffraction light (+ first order or − first order diffraction light) which are produced from a micro fine pattern on the inspected object and entered into the pupil of the objective lens, control the annular-looped illumination (for example, OUT σ and IN σ) according to this identified (observed or detected) locality distribution of the diffraction light, apply this controlled annular-looped illumination to the micro fine pattern on the inspected object to detect image signals of a high resolution (resolution power) adapted to the micro fine pattern, compare this high resolution image signal with the reference high resolution image signal, and erase the micro fine pattern according to consistency of these image signals to detect the defects on the micro fine pattern and therefore provides an effect enabling to inspect the defects on the micro fine patterns in high reliability.

Further, the present invention is adapted to detect image signals with a high resolution (resolution power) adapted to a micro fine pattern by detecting an image showing a density of the micro fine pattern based on the diffraction light which is produced from the micro fine pattern on the inspected object and entered into the pupil of the objective lens, controlling the annular-looped illumination (for example, OUT σ and IN σ) according to this image, and applying this controlled annular-looped illumination to the micro fine pattern on the inspected object, and by comparing this high resolution image signal with the reference high resolution image signal and erasing the micro fine pattern according to consistency of these image signals to detect the defects on the micro fine pattern and therefore provides an effect enabling to inspect the defects on the micro fine patterns in high reliability.

While we have shown and described several embodiments in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

What is claimed is:

1. A method for detecting information relating to a pattern on an object to be inspected comprising the steps of:

focusing and irradiating an annular-looped diffusion illumination light formed with a plurality of virtual spot light sources onto a pattern on the object to be inspected through a pupil of an objective lens;

receiving an image of the pattern of the inspected object by focusing a first or second order diffraction light including a 0th order diffraction light which is reflected from the pattern on the inspected object by the focused and irradiated annular-looped diffusion illumination light and entered into the pupil of the objective lens;

monitoring the image received into the pupil of the objective lens and controlling the annular-looped diffusion illumination light in response thereto: and converting the received image of the pattern of the inspected object to image signals of the pattern for obtaining information relating to the pattern.

2. A method according to claim 1, wherein the image signals of the pattern provide information relating to a defect of the pattern.

3. A method according to claim 1, wherein the step of receiving an image of the pattern includes utilization of an image sensor, and further comprising the steps of comparing the image signals of the pattern of the inspected object with image signals of a reference pattern, erasing the pattern of the inspected object according to consistency of the received image signals and the image signals of the reference pattern, and detecting a defect of the pattern according to an inconsistency.

4. A method according to claim 3, further comprising the steps of receiving with the image sensor an image of an impurity on the pattern on the inspected object obtained by focusing a scattering light which is reflected from an impurity on the inspected object with a dark field illumination irradiated onto the pattern on the inspected object and entered into the pupil of the objective lens, converting the received image to the signals indicating the impurity, and detecting impurity information of the pattern.

5. A method according to claim 1, wherein at least one of the step of focusing and irradiating and the step of receiving includes utilizing a light quantity control filter for partly changing an intensity or a quantity of the first or second order diffraction light including a 0th order diffraction light entered into the pupil of the objective lens and reflected from the pattern, the step of receiving further includes utilizing an image sensor, and further comprising detecting the pattern on the inspected object according to the converted image signals of the pattern.

6. A method according to claim 5, further comprising the steps of comparing the converted image signals of the pattern with image signals of a reference pattern, erasing the pattern of the inspected object according to consistency of the received image signals and the image signals of the reference pattern, and detecting a defect according to an inconsistency.

7. A method according to claim 5, wherein the step of receiving includes utilizing a first image sensor, and the step of controlling the annular-looped diffusion illumination light according to image signals of the pupil obtained by receiving the image into the pupil of the objective lens includes utilizing a second image sensor.

8. A method according to claim 7, further comprising the step of converting the image received by the second image sensor.

9. A method according to claim 7, wherein the step of controlling include receiving with the second image sensor the image of a distribution of a locality of the diffraction lights including the 0th order diffraction light entered into the pupil of the objective lens.

10. A method according to claim 9, further comprising the steps of comparing the image signals of the pattern obtained from the first image sensor with image signals of a reference pattern, erasing the pattern of the inspected object according to consistency of the image signals obtained from the first image sensor with the image signals of the reference pattern, and detecting a defect of the pattern according to inconsistency of the compared image signals.

11. A method according to claim 7, further comprising the steps of comparing the image signals of the pattern obtained from the first image sensor with image signals of a reference pattern, erasing the pattern of the inspected object according to consistency of the image signals received by the first image sensor and the image signals of the reference pattern, and detecting a defect of the pattern according to inconsistency of the compared image signals.

12. A method according to claim 1, further comprising the step of detecting the pattern on the object to be inspected according to the converted image signals of the pattern.

13. A method according to claim 1, wherein the step of focusing and irradiating includes focusing and irradiating a polarization annular-looped diffusion illumination light formed by adding a polarization to the annular-looped diffusion illumination light formed with the plurality of virtual spot light sources onto the pattern, and detecting the pattern on the object to be inspected according to the image signals of the pattern.

14. A method according to claim 13, wherein the polarization is one of circular and elliptical polarization.

15. A method according to claim 1, wherein the step of focusing and irradiating includes focusing and irradiating a polarization annular-looped diffusion illumination light formed by adding a polarization to the annular-looped diffusion illumination light formed with the plurality of virtual spotlight sources onto the pattern, and further comprising the steps of comparing the image signals of the pattern of the inspected object with image signals of a reference pattern, erasing the pattern of the inspected object according to consistency of the image signals of the pattern and the image signals of the reference pattern, and detecting a defect of the pattern according to inconsistency of the compared image signals.

16. A method according to claim 15, wherein the polarization is one of circular and elliptical polarization.

17. A semiconductor substrate manufacturing method for manufacturing semiconductor substrates respectively having a pattern or patterns in a manufacturing line comprising various process units, comprising the steps:

performing history data or data based build-up by accumulating in advance of a present step of manufacturing information of a pattern defect which occurred on the semiconductor substrate and history data or a data base which indicates a correlation between a defect and a cause of defect or a factor of defect which incurs a defect of a pattern in the manufacturing line and building up the history data or the database which indicates the correlation;

performing defect inspection utilizing the method according to claim 1 for detecting defect information of a pattern on an inspected object which is a semiconductor substrate, wherein the focused and irradiated annular-looped diffusion illumination light is irradiated to the semiconductor substrate which reaches a specified position on the manufacturing line, obtaining the converted image signals and comparing the received converted image signals of the pattern with image signals of a reference pattern for detecting defect information;

analyzing a cause of a defect or a factor of a defect which incurs a defect of the pattern in an upstream manufacturing line from the specified position of the manufacturing line according to the information of the pattern defect which occurs on the semiconductor substrate as detected and the history data or the database which is built up in the history data or database built-up step and indicates a correlation between the information of a pattern defect and a cause of a defect or a factor of a defect; and controlling process conditions in the upstream manufacturing line for eliminating the cause of a defect or the factor of the defect which has been analyzed in the defect cause analyzing step.

18. A semiconductor substrate manufacturing method according to claim 17, wherein the inspection step includes controlling the annular-looped diffusion illumination light focused and irradiated onto the pattern on the semiconductor substrate, and receiving a high resolution image of the pattern.

19. A semiconductor substrate manufacturing method according to claim 17, wherein in the inspection step, the annular-looped diffusion illumination light which is focused and irradiated is a polarized annular-looped diffusion illumination light formed by adding polarization to the annular-looped diffusion light.

20. A semiconductor substrate manufacturing method according to claim 19, wherein in the inspection step, the polarized annular-looped diffusion light is one of circular and elliptical polarization.

21. A semiconductor substrate manufacturing method according to claim 17, further comprising an impurity inspection step for detecting an impurity on the pattern by irradiating a dark field illumination onto the semiconductor substrate which has reached the specified position on the manufacturing line, receiving an image of an impurity of the pattern of the inspected object obtained by focusing a scattering light which is reflected from an impurity on the pattern of the inspected object and entered into the pupil of the objective lens with an image sensor, and converting the received image signals indicating the impurity, the analyzing step including analyzing a cause of at least one of a defect and impurity or a factor of at least one of a defect or impurity which incurs a defect or an impurity of the pattern in the upstream manufacturing line from the specified position of the manufacturing line in accordance with the defect information of the pattern detected in the defect inspection step and the impurity information of the pattern detected in the impurity inspection step and the history data or the data base which is built up in the history data or data base buildup step and indicates the correlation of causes and results, and the controlling process conditions step includes controlling process conditions in the upstream manufacturing line for eliminating the cause of at least one of the defect and impurity or a factor of at least one of the defect and impurity analyzed in the at least one of the defect and impurity cause analyzing step.

22. A pattern detection apparatus for detecting a pattern on an object to be inspected, comprising:

illumination means for emitting an annular-looped diffusion illumination light formed with a plurality of virtual spot light sources;

an illumination optical system for focusing and irradiating the emitted annular-looped diffusion light onto a pattern on an inspected object through a pupil of an objective lens;

a detection optical system for receiving with an image sensor, an image of the pattern on the inspected object obtained by focusing a first or second order diffraction light including a 0th order diffraction light which is reflected from the pattern on the inspected object by the focused and irradiated-annular-looped diffusion illumination light from the illumination optical system and entered into the pupil of the object lens, and for converting the received image of the pattern to image signals of the pattern for obtaining information relating to the pattern;

a pupil detection optical system for receiving with another image sensor, the image on the pupil of the objective lens from the another image sensor and for converting a received image to image signals of the pupil; and control means for controlling the annular-looped diffusion illumination light emitted by the illumination means according to the image signals of the pupil obtained from the another image sensor of the pupil detection optical system.

23. A pattern detection apparatus according to claim 22, further comprising comparison means for comparing the converted image signals of the pattern with image signals of a reference pattern;

means for erasing the pattern of the inspected object according to consistency of the received converted image signals and the image signals of the reference pattern; and means for detecting a defect according to an inconsistency.

24. A pattern detection apparatus according to claim 23, wherein at least one of the illumination optical system and the detection optical system includes a light quantity control filter for partly changing the intensity or the light quantity of the first or second order diffraction light, including the 0th order diffraction light which is reflected from the pattern.

25. A pattern detection apparatus according to claim 24, wherein the detection optical system includes the light quantity control filter for partly controlling the light quantity of the 0th order diffraction light which is reflected from the pattern.

26. A pattern detection apparatus according to claim 22, wherein the detection optical system includes means for varying optical magnification therein.

27. A pattern detection apparatus according to claim 22, wherein the illumination optical system includes polarization means having polarization conversion optical elements for adding polarization to the annular-looped diffusion illumination light emitted from the illumination means.

28. A pattern detection apparatus according to claim 27, wherein the polarization means includes one of circular and elliptical polarization conversion optical elements for applying one of circular and elliptical polarization to the emitted annular-looped diffusion illumination light.

29. A pattern detection apparatus according to claim 22, further comprising another illumination optical system for irradiating a focused dark field illumination to the pattern on the inspected object, another detection optical system for receiving light from an impurity on the pattern on the inspected object obtained by focusing a scattering light which is reflected from the pattern on the inspected object irradiated by the another illumination optical system and entered into the pupil of the objective lens, and for converting the received light to signals indicative of the impurity, and further comprising comparison means for comparing the image signals of the pattern obtained from the detection optical system with image signals of a reference pattern, means for erasing the pattern of the inspected object according to consistency of the image signals of the pattern and image signals of the reference pattern, and means for detecting a defect of a pattern according to an inconsistency, and impurity detection means for detecting impurity information according to the signal obtained from the another detection optical system.

30. A pattern detection apparatus according to claim 29, wherein the illumination optical system includes polarization means for adding polarization to the annular-looped diffusion illumination light emitted by the illumination means and including polarization conversion optical elements.

31. A pattern detection apparatus according to claim 30, wherein the polarization means includes means for adding one of circular and elliptical polarization and including one of circular and elliptical polarization conversion optical elements.

32. A pattern detection apparatus according to claim 22, wherein the pattern detection apparatus is part of a microscope system.

33. A pattern detection apparatus according to claim 22, wherein the pattern detection apparatus is part of a manufacturing system for manufacturing semiconductors and the object to be inspected is a semiconductor substrate having the pattern thereon.

34. A pattern detection inspection apparatus according to claim 22, wherein the detection optical system includes means for enabling variable optical magnification therein.

35. A pattern detection apparatus for detecting a pattern on an object to be inspected comprising:

illumination means for emitting an annular-looped diffusion illumination light formed with a plurality of virtual spot light sources:

an illumination optical system for focusing and irradiating the emitted annular-looped diffusion light onto a pattern on an inspected object through a pupil of an objective lens; and a detection optical system for receiving with an image sensor, an image of the pattern on the inspected object obtained by focusing a first or second order diffraction light including a 0th order diffraction light which is reflected from the pattern on the inspected object by the focused and irradiated annular-looped diffusion illumination light from the illumination optical system and entered into the pupil of the object lens, and for converting the received image of the pattern to image signals of the pattern for obtaining information relating to the pattern, a pupil detection optical system for receiving with another image sensor a distribution of locality of diffraction light including the 0th order diffraction light and for converting the received image to image signals of the pupil; and control means for controlling the annular-looped diffusion illumination light emitted by the illumination means according to the image signals of the pupil obtained from the another image sensor of the pupil detection optical system.

36. A pattern detection apparatus according to claim 35, wherein the detection optical system includes means for varying an optical magnification therein.

37. A pattern defect inspection apparatus for detecting a defect of a pattern on an object to be inspected comprising:

illuminating means for irradiating a uniform illumination light in a detection field of an object to be inspected through an objective lens;

image detection means for detecting and converting a reflected light from the inspected object to an image by photoelectric conversion;

image comparison means for comparing the detection image with a reference image;

a pupil detection optical system for receiving with an image sensor, the image on a pupil of the objective lens and for converting a received image to image signals of the pupil; and control means for controlling the uniform illumination light emitted by the illuminating means according to the image signals of the pupil obtained from the image sensor of the pupil detection optical system.

38. A pattern defect inspection apparatus according to claim 37, further comprising polarization state control means for controlling a state of polarization of the illumination light emitted by the illuminating means.

* * * * *